(12) United States Patent
Bonnette et al.

(10) Patent No.: US 7,879,022 B2
(45) Date of Patent: Feb. 1, 2011

(54) RAPID EXCHANGE FLUID JET THROMBECTOMY DEVICE AND METHOD

(75) Inventors: Michael J. Bonnette, Minneapolis, MN (US); Michael P. Schrom, Wyoming Township, MN (US); Hieu V. Le, Brooklyn Park, MN (US)

(73) Assignee: MEDRAD, Inc., Indianola, PA (US)

( * ) Notice: Subject to any disclaimer, the term of this patent is extended or adjusted under 35 U.S.C. 154(b) by 1522 days.

(21) Appl. No.: 11/096,592

(22) Filed: Apr. 1, 2005

(65) Prior Publication Data

US 2006/0064123 A1 Mar. 23, 2006

Related U.S. Application Data

(60) Continuation-in-part of application No. 10/198,264, filed on Jul. 16, 2002, now Pat. No. 6,875,193, which is a continuation-in-part of application No. 09/888,455, filed on Jun. 25, 2001, now Pat. No. 6,755,803, which is a continuation-in-part of application No. 09/356,783, filed on Jul. 16, 1999, now abandoned, which is a division of application No. 09/019,728, filed on Feb. 6, 1998, now Pat. No. 5,989,210.

(51) Int. Cl.
*A61M 3/00* (2006.01)
*A61M 25/00* (2006.01)

(52) U.S. Cl. .......................... 604/526; 604/43

(58) Field of Classification Search .................... 604/43, 604/523–527
See application file for complete search history.

(56) References Cited

U.S. PATENT DOCUMENTS

| 1,902,418 | A | 3/1933 | Pilgrim |
| 3,752,617 | A | 8/1973 | Burlis et al. |
| 3,930,505 | A | 1/1976 | Wallach |

(Continued)

FOREIGN PATENT DOCUMENTS

DE 3705339 9/1988

(Continued)

OTHER PUBLICATIONS

European Search Report for corresponding application EP 99300846.

(Continued)

*Primary Examiner*—Nicholas D Lucchesi
*Assistant Examiner*—Nathan R Price
(74) *Attorney, Agent, or Firm*—David J. Schramm

(57) ABSTRACT

A rapid exchange fluid jet thrombectomy device having a streamlined manifold and a catheter having multiple tubular segments where each tubular segment increases in flexibility in a distal direction. Torque response and pushability is enhanced by the arrangement of a proximally located tubular segment composed of a polymer-jacketed spiral metal tube in combination with an intermediate tubular section and a distal tubular section each having different degrees of flexibility. A guidewire tube exit region is provided where the intermediate tubular section joins the distal tubular section for over-the-wire guidewire usage. The polymer-jacketed spiral metal tube can extend along a partial or full length of the catheter and can include a basic continuous spiral cut which has regions of constant pitch or which has progressively increasing pitch, or in the alternative, can include an interlocking spiral cut having constant pitch regions or progressively decreasing pitch.

16 Claims, 28 Drawing Sheets

U.S. PATENT DOCUMENTS

| | | | |
|---|---|---|---|
| 4,224,943 A | 9/1980 | Johnson et al. |
| 4,248,234 A | 2/1981 | Assenza et al. |
| 4,290,428 A | 9/1981 | Durand et al. |
| 4,328,811 A | 5/1982 | Fogarty |
| 4,385,635 A | 5/1983 | Ruiz |
| 4,631,052 A | 12/1986 | Kensey |
| 4,636,346 A | 1/1987 | Gold et al. |
| 4,690,672 A | 9/1987 | Veltrup |
| 4,739,768 A | 4/1988 | Engelson |
| 4,747,405 A | 5/1988 | Leckrone |
| 4,781,186 A | 11/1988 | Simpson et al. |
| 4,782,834 A | 11/1988 | Maguire et al. |
| 4,790,813 A | 12/1988 | Kensey |
| 4,842,579 A | 6/1989 | Shiber |
| 4,883,459 A | 11/1989 | Calderon |
| 4,888,146 A | 12/1989 | Dandeneau |
| 4,898,574 A | 2/1990 | Uchiyama et al. |
| 4,898,591 A | 2/1990 | Jang et al. |
| 4,902,276 A | 2/1990 | Zakko |
| 4,913,698 A | 4/1990 | Ito et al. |
| 4,950,238 A | 8/1990 | Sullivan |
| 5,011,469 A | 4/1991 | Buckberg et al. |
| 5,085,649 A | 2/1992 | Flynn |
| 5,086,842 A | 2/1992 | Cholet |
| 5,092,873 A | 3/1992 | Simpson et al. |
| 5,114,399 A | 5/1992 | Kovalcheck |
| 5,135,482 A | 8/1992 | Neracher |
| 5,163,431 A | 11/1992 | Griep |
| 5,215,614 A | 6/1993 | Wijkamp |
| 5,221,270 A | 6/1993 | Parker |
| 5,234,416 A | 8/1993 | Macaulay et al. |
| 5,250,059 A | 10/1993 | Andreas et al. |
| 5,254,107 A | 10/1993 | Soltesz |
| 5,259,842 A | 11/1993 | Plechinger et al. |
| 5,273,526 A | 12/1993 | Dance et al. |
| 5,300,022 A | 4/1994 | Klapper et al. |
| 5,308,342 A | 5/1994 | Sepetka et al. |
| 5,318,518 A | 6/1994 | Plechinger et al. |
| 5,320,599 A | 6/1994 | Griep et al. |
| 5,324,285 A | 6/1994 | Cannon |
| 5,342,386 A | 8/1994 | Trotta |
| 5,358,485 A | 10/1994 | Vance et al. |
| 5,370,609 A | 12/1994 | Drasler et al. |
| 5,372,601 A | 12/1994 | Lary |
| 5,380,307 A | 1/1995 | Chee et al. |
| 5,399,164 A | 3/1995 | Snoke et al. |
| 5,425,723 A | 6/1995 | Wang |
| 5,456,674 A | 10/1995 | Bos et al. |
| 5,478,330 A | 12/1995 | Imran et al. |
| 5,496,267 A | 3/1996 | Drasler et al. |
| 5,496,294 A | 3/1996 | Hergenrother et al. |
| 5,499,973 A | 3/1996 | Saab |
| 5,531,685 A | 7/1996 | Hemmer et al. |
| 5,542,924 A | 8/1996 | Snoke et al. |
| 5,554,121 A | 9/1996 | Ainsworth et al. |
| 5,571,094 A | 11/1996 | Sirhan |
| 5,599,325 A | 2/1997 | Ju et al. |
| 5,624,397 A | 4/1997 | Snoke et al. |
| 5,634,897 A | 6/1997 | Dance et al. |
| 5,658,263 A | 8/1997 | Dang et al. |
| 5,662,622 A | 9/1997 | Gore et al. |
| 5,676,659 A | 10/1997 | McGurk |
| 5,681,336 A | 10/1997 | Clement et al. |
| 5,683,345 A | 11/1997 | Waksman et al. |
| 5,687,714 A | 11/1997 | Kolobow et al. |
| 5,702,439 A | 12/1997 | Keith et al. |
| 5,704,926 A | 1/1998 | Sutton |
| 5,713,849 A | 2/1998 | Bosma et al. |
| 5,769,828 A * | 6/1998 | Jonkman ................ 604/526 |
| 2005/0059957 A1 * | 3/2005 | Campbell et al. ........... 604/524 |

FOREIGN PATENT DOCUMENTS

| | | |
|---|---|---|
| DE | 3421390 | 6/1994 |
| EP | 0251512 | 1/1988 |
| EP | 0232678 | 8/1992 |
| EP | 0528181 | 2/1993 |
| EP | 1382366 A1 * | 1/2004 |
| GB | 1571459 | 7/1980 |
| WO | WO9005493 | 5/1990 |
| WO | WO9410917 | 5/1994 |

OTHER PUBLICATIONS

International Search Report for corresponding application PCT/US05/41412.

* cited by examiner

RAPID EXCHANGE FLUID JET THROMBECTOMY DEVICE AND METHOD

CROSS REFERENCES TO RELATED APPLICATIONS

This patent application is a continuation-in-part of Ser. No. 10/198,264 entitled "Rapid Exchange Fluid Jet Thrombectomy Device And Method" filed on Jul. 16, 2002 now U.S. Pat. No. 6,875,193, which is a continuation-in-part of Ser. No. 09/888,455 entitled "Single Operator Exchange Fluid Jet Thrombectomy Device" filed on Jun. 25, 2001, now U.S. Pat. No. 6,755,803, which is a continuation-in-part of Ser. No. 09/356,783 entitled "Rheolytic Thrombectomy Catheter and Method of Using Same" filed on Jul. 16, 1999, abandoned, which is a divisional of Ser. No. 09/019,728 entitled "Rheolytic Thrombectomy Catheter and Method of Using Same" filed on Feb. 6, 1998, now U.S. Pat. No. 5,989,210.

This patent application is also related to Ser. No. 09/417,395 entitled "Thrombectomy Catheter and System" (as amended) filed on Oct. 13, 1999, now U.S. Pat. No. 6,676,627, which is a continuation-in-part of Ser. No. 08/349,665 entitled "Thrombectomy Method" filed on Dec. 5, 1994, now U.S. Pat. No. 6,558,366, which is a divisional of Ser. No. 08/006,076 entitled "Thrombectomy Device" filed on Jan. 15, 1993, now U.S. Pat. No. 5,370,609, which is a continuation of Ser. No. 07/563,313 entitled "Thrombectomy Method and Device" filed on Aug. 6, 1990, abandoned.

This patent application is also related to Ser. No. 08/351,605 entitled "Thrombectomy and Tissue Removal Method" filed on Dec. 8, 1994, now U.S. Pat. No. 6,471,683, which is a divisional of Ser. No. 07/976,367 entitled "Thrombectomy and Tissue Removal Method and Device" filed on Nov. 13, 1992, abandoned, which is a continuation-in-part of Ser. No. 07/563,313 entitled "Thrombectomy Method and Device" filed on Aug. 6, 1990, abandoned.

BACKGROUND OF THE INVENTION

Field of the Invention

The present invention relates to apparatus for use in treatment of the human body. More particularly, the present invention relates to an elongated device which may be a single component catheter assembly or a multiple component catheter assembly and which is suitable for use through percutaneous or other access, for endoscopic procedures, or for intraoperative use in either open or limited access surgical procedures. Still more particularly, the present invention relates to an elongated device in the form of a fluid jet thrombectomy catheter, being adapted for fragmentation and removal of thrombus or other unwanted material from blood vessels or body cavities by using high velocity saline (or other suitable fluid) jets to macerate the thrombus or other unwanted material. The elongated device bears certain similarities to a previously described water jet thrombectomy catheter device and can be used as such, but differs therefrom in several material respects, major differences being the construction of the device from simpler components, and enhanced utility of the device in rapid exchange methods with a single operator.

A streamlined manifold seals around a threaded high pressure connection port via adhesive injected into a port which is then cured by UV light as opposed to effecting a seal by compression of a high pressure connector via a compressive nut. This modification eliminates a nut as a component. The opposing end of the manifold seals around a proximal end of a proximal tube via adhesive injected into a port which is then cured by UV light to bond the proximal end of the proximal tube to the manifold as opposed to effecting a seal by compression of a strain relief around the proximal end of the proximal tube and against the manifold via a compressive nut. Such a construction eliminates a nut as a component and also eliminates or minimizes adhesive applied in other fashions on various regions of the strain relief, which in previous constructions proved to be difficult to bond reliably with low bond strengths. The present invention utilizes a tapered and flexible strain relief which provides much more adequate strain relief due to it gradual tapered design. In addition to this, verbiage specifying mode of operation, French size, or other information can be pad printed on the strain relief instead of being molded directly therein, thereby greatly improving information application and the visibility of the information.

Another major difference involves a connected and substantially continuous multiple section catheter having a proximal tube and featuring a guidewire tube exit region between a distally located formed tubular portion of an intermediate tube and the proximal end of a distal tube to facilitate transition between a guidewire-containing and a non-guidewire-containing portion of the catheter. The proximal tube consists of a polymer-jacketed continuous spiral metal tube which can be laser cut which provides for excellent pushability that is superior to previous designs and which is also less kinkable and more flexible than previous designs. The spiral cut can be varied in pitch from distal to proximal to produce a continuous transition from flexible to stiff which maximizes the pushability and "feel" of the catheter. The laser cut or otherwise suitably formed spiral metal tube can be of different configurations to achieve the desired property. The length, the pitch and the spacing of the spiral cut along the spiral metal tube can be varied anywhere along the length of the catheter whether just in the proximal tube, as shown in a first embodiment, or along the entire length of the catheter including the intermediate tube and the distal tube to provide a desired mechanical property, as shown in one or more alternative embodiments. In effect, there are four zones of transition with respect to flexibility along the catheter: the proximal tube with the proximal tube being of continuous transition due to the variation of the spiral metal tube, the intermediate tube, the distal tube, and the tip extension tube. The entire catheter could be of a one-piece design with the polymer-jacketed spiral metal tube having inflow and outflow orifices cut into the spiral metal tube. The polymer jacket exterior to the metal spiral tube creates a leak-free spiral metal tube and adds to the mechanical and lubricious properties of the catheter.

The intermediate tube, an added transitional midsection in the catheter, improves overall transition from the distally located tapered tip to the proximal end of the catheter, whereas the previous design has no such intermediate transition. Additionally, the semi-rigid metal tube of the previous design, which aligned to a guidewire tube, is also no longer incorporated to provide for guidewire tube exit structure but is replaced by a plastic intermediate tube which can be of a harder durometer material than the material of the distal tube. The plastic intermediate tube can be attached over the spiral metal tube of the proximal tube via adhesive and/or a heat bond to provide for guidewire tube exit region structure.

A guidewire tube exit region created from reflowing three different polymer tubes together consists of the junction of the distal tube, the intermediate tube, and a guidewire tube forming a guidewire exit region by the use of a Teflon®-coated, specially shaped mandrel (not shown). In addition to this, the flexibility of the all plastic guidewire tube exit region provides for a more smooth transition for guidewire movement.

A reconfigured tip consists of joining a softer piece of a polymeric tip extension tube about the distal end of the guidewire tube and within the lumen of the distal tapered tip, distal to the cross stream orifices, to provide a smooth transition from one section to the next via a heat bond or fusion of the two plastics. The previous tip was formed solely and directly from the distal tube. The new tip is tapered to a smaller crossing profile also. The tapered tip, the guidewire tube, and the tip extension tube are also joined more robustly since they also are heat bonded during the tip formation process.

The device is particularly advantageous in a cross stream configuration but can be adapted to other forms as well. The cross stream jets create a recirculation flow pattern optimized for clearing a large cross section of mural thrombus or other similar material. Further, the present invention also relates to a system constituted either by the combination of the device with both pressurized fluid source means and exhaust regulation means or by the combination of the device with only pressurized fluid source means. Other ancillary devices or features can be utilized or incorporated, such as introduction devices, guiding devices, isolation or filtering devices, centering devices, imaging devices, infusion or withdrawal devices, dilatation devices, energy delivery devices, and so forth, to aid in diagnosis or treatment of a patient, without departing from the scope of the present invention. The intermediate tube which includes the guidewire tube exit region can be applied to other catheters such as intravascular catheters, balloon catheters, device delivery catheters, and so forth, and is not limited solely to fluid jet material removal catheters.

SUMMARY OF THE INVENTION

The present invention, a rapid exchange fluid jet thrombectomy device and method, involves a medical device for removal of material such as thrombus from a vessel or other body cavity. As shown in one or more embodiments, the rapid exchange fluid jet thrombectomy device can function as a rheolytic thrombectomy catheter for removing tissue from a vessel or other body cavity.

A catheter according to the present invention has a high pressure lumen which carries pressurized working fluid such as saline solution from the proximal end to the distal end which has a jet emanator, where the working fluid exits to form one or more high velocity fluid jets. When the high velocity jets are operating, blood, thrombus, or other fluid or unwanted material is drawn in through inflow orifices into a distal tube due to a low pressure zone created by the high velocity fluid jets. Further, proximal to this low pressure zone, the distal tube thereby becomes somewhat pressurized, with the pressure being able to drive fluid and unwanted material proximally along the distal tube. Preferably, there are one or more outflow orifices in the pressurized region of the distal tube, so that a portion of the fluid and unwanted material (which has been broken into small pieces by the high velocity fluid jets) passes out from the distal tube into the body vessel or cavity in which the catheter has been placed, creating one or more "cross stream" jets with radial componency. These cross stream jets act to break unwanted material off the surface of the body vessel or cavity and aid in creating a fluid recirculation pattern for more effective removal of unwanted material. The basic design of the rapid exchange fluid jet catheter could function without separate outflow orifices, but these outflow orifices, being separate from inflow orifices, provide a more efficient and effective removal of unwanted material. A separate guidewire tube inside the distal tube provides for passage of a guidewire through a tip extension tube at the distal tapered tip of the distal tube and out the proximal end of the distal tube at a location known as a guidewire tube exit region. The distal end of the catheter utilizes the tapered tip and tip extension tube to better approximate the diameter of the guidewire and to provide better passage within the body vessel or cavity or past a tight stenosis or lesion. The proximal portion of the rapid exchange fluid jet catheter has a proximal tube which contains a guidewire lumen which does not house a guidewire or a guidewire tube. At the proximal end of the catheter, there is a streamlined manifold which includes a high pressure connection port and an exhaust branch or, alternatively, a continuous line to a waste collection chamber via a pump. The distal tube typically extends less than half the length of the catheter, and the proximal tube typically extends greater than half the length of the catheter.

Interposed between the proximal tube, consisting of co-located spiral metal tube and flexible polymer material, and the distal tube of flexible polymer is a relatively short intermediate tube, preferably of a polymer. The intermediate tube is round at its proximal end to fit snugly inside and attach to the distal end of the proximal tube. The intermediate tube is formed or otherwise constructed to have a truncated and rounded slot which is shallower toward the proximal end and deeper toward the distal end. This truncated and rounded slot is sized so that the guidewire tube will accommodatingly fit along the truncated and rounded slot at the distal end, and the intermediate tube is formed so that the truncated and rounded slot region fits snugly inside the proximal end of the distal tube. The proximal end of the guidewire tube is located along the truncated and rounded slot of the intermediate tube, and preferably near the proximal end of the distal tube. The guidewire tube is positioned and sized so that a guidewire can pass through the distal end of the guidewire tube located at or near the distal tapered tip and tip extension tube of the catheter, through the length of the guidewire tube to exit the guidewire tube through the guidewire tube exit region located at the junction of the proximal end of the distal tube and the distal end of the intermediate tube. The high pressure lumen connects to the high pressure connection port or can run all the way to a pump located proximally of the manifold, and passes within the proximal tube, the intermediate tube and the distal tube. Adhesive sealant may be used to bond the various components to one another to provide fluid seals between components. Alternatively, thermal bonding or heat-shrinking can be used; or the components may be sized to form a tight, secure fit without additional bonding.

The present invention also includes a design of an intermediate tube for a rapid exchange catheter, which may be a fluid jet catheter, a balloon catheter, or other diagnostic or treatment catheter.

The present invention also includes a rapid exchange fluid jet catheter system incorporating a rapid exchange fluid jet catheter, a high pressure fluid source, and a collection system with optional exhaust regulation means, where a guidewire passes through only the distal portion of the rapid exchange fluid jet catheter.

The present invention also includes a method of fabricating such a rapid exchange catheter utilizing an intermediate tube. The method includes the steps of:

a. providing a proximal tube consisting of co-located flexible spiral metal tubing and flexible polymer jacket, a distal tube, a guidewire tube, and an intermediate tube with a truncated and rounded slot which is deeper at the distal end than at the proximal end thereof;

b. fitting the distal end of the proximal tube to the proximal end of the intermediate tube, and fitting the proximal end of the distal tube to the distal end of the intermediate tube; and, c. positioning the guidewire tube so that it extends along the length of the distal tube and terminates at or near the distal end of the distal tube, and extends proximally to a point along the truncated and rounded slot of the intermediate tube, thereby providing communication for passage from the outside of the rapid exchange catheter at the distal end of the guidewire tube located at or near the distal tapered tip of the catheter, through the length of the distal tube; i.e., through the guidewire tube, and then exiting through the proximal end of the distal tube at a location (guidewire tube exit region) near the distal end of the intermediate tube.

The above embodiment of the present invention also provides a method of removing thrombus or other unwanted material from a body vessel or cavity. The method includes the steps of:

a. providing a guidewire and rapid exchange fluid jet catheter including a manifold, a proximal tube consisting of co-located flexible spiral metal tubing and flexible polymer jacket, a distal tube, an intermediate tube, a guidewire tube, a high pressure lumen, a guidewire tube exit region, a proximal high pressure connection port, and a distal fluid jet emanator;

b. advancing the guidewire through the vasculature and past the vascular site containing thrombus or other unwanted material;

c. introducing the rapid exchange fluid jet catheter by passing the proximal end of the guidewire through the distal end of the guidewire tube and advancing the rapid exchange fluid jet catheter along the guidewire to the site containing thrombus or other unwanted material; and, d. providing a high pressure supply of saline or other fluid to the high pressure lumen via the proximal high pressure connection port or direct connection to a pump so as to cause at least one high velocity fluid jet to emanate from the fluid jet emanator and to entrain thrombus or other unwanted material into the distal tube via an inflow orifice where the thrombus or other unwanted material is macerated and propelled proximally along the distal tube, intermediate tube, and proximal tube for removal from the body, while either maintaining a positive or negative fluid balance at the distal tip.

The method of removing thrombus or other unwanted material from a body vessel or cavity preferably includes providing a distal tube with outflow orifices, which create cross stream jets for enhanced removal of material.

According to one or more embodiments of the present invention, there is provided a rapid exchange fluid jet thrombectomy device, including a manifold including a connection port and other devices, a proximal tube consisting of co-located flexible spiral metal tubing and a flexible polymer jacket extending distally from the manifold, an intermediate tube extending distally from the proximal tube, a truncated and rounded slot extending along a distal portion of the intermediate tube, a distal tube extending distally from the intermediate tube, an accessible guidewire tube accommodated by and extending along and from a portion of the truncated and rounded slot into and along the greater portion of the distal tube, a fluid jet emanator connected to a high pressure tube extending from the manifold through the proximal tube, the intermediate tube, and the distal tube, and a plurality of inflow and outflow orifices located at the distal end of the distal tube at a location proximal to a flexible tapered tip and a soft tip extension tube.

One significant aspect and feature of the present invention is a rapid exchange fluid jet thrombectomy device which can be operated by one practitioner.

Another significant aspect and feature of the present invention is a rapid exchange fluid jet thrombectomy device having inflow orifices and outflow orifices to create cross stream jets.

Still another significant aspect and feature of the present invention is a guidewire tube for passage of a guidewire through the distal portion of the device.

Yet another significant aspect and feature of the present invention is an intermediate tube to provide connection between a proximal tube, a distal tube, and a guidewire tube at a guidewire exit region.

A further significant aspect and feature of the present invention is an easier method of utilizing a fluid jet catheter due to a unitary design.

A still further significant aspect and feature of the present invention is the ability to incorporate various fluid jet emanator shapes, styles and designs.

An additional significant aspect and feature of the present invention is the reduction of fabrication costs by eliminating complicated extruded shapes, minimizing the number of components, reducing the complexity of the components, and improving the quality of the components.

Another significant aspect and feature of the present invention is the inclusion of structural members which allow minimizing the outer diameter of the device while maximizing the inner diameter of the device. The outer diameter of the device is minimized to provide the least intrusive profile and the inside diameter of the device is maximized for higher and less restrictive exhaust flow.

A yet further significant aspect and feature of the present invention is coating the device hydrophilically for improved movement along a guidewire, as well as improved trackability.

Another significant aspect and feature of the present invention is the incorporation of a tube support ring and the structure of a fluid jet emanator in conjunction with marker bands to provide for stabilization of the inflow and outflow orifices when passed through tortuous vascular paths, as well as to provide for the ability to be suitably detected by fluoroscopic identifying measurement devices.

Another significant aspect and feature of the present invention is a manifold which reduces the number of components and provides superior sealability and bond strengths.

Another significant aspect and feature of the present invention is a superior strain relief.

Another significant aspect and feature of the present invention is the use of a catheter having a proximal tube consisting of a polymer-jacketed spiral metal tube to provide superior pushability and trackability with a minimal wall thickness and to provide superior handling characteristics while maintaining the smallest wall thickness possible, thereby providing devices of smaller cross section.

Another significant aspect and feature of the present invention is a proximal tube consisting of a polymer-jacketed spiral metal tube with the spiral metal tube being a basic continuous spiral which may occur in groups of constant pitch or in progressive pitch along the length of the spiral metal tube to provide a continuous pitch transition.

Another significant aspect and feature of the present invention is a proximal tube consisting of a polymer-jacketed spiral metal tube with the spiral cut being a complicated jigsaw type spiral which may occur in groups of constant pitch or in progressive pitch along the length of the spiral metal tube to provide a continuous pitch transition and interlock to provide superior torqueability and other handling characteristics.

Another significant aspect and feature of the present invention is the extension of a polymer-jacketed spiral metal tube for any portion of the catheter at any position along the entire length of the catheter, or along multiple separated or joined positions.

Another significant aspect and feature of the present invention is the use of an intermediate tube which is of a softer durometer than the proximal tube and a harder durometer than the distal tube.

Another significant aspect and feature of the present invention is the use of an all plastic guidewire exit port region which can be located anywhere from 2-38 cm from the tapered tip, but preferably about 25 cm from the tapered tip.

Another significant aspect and feature of the present invention is the use of polymer tubing within and extending from the tapered tip which is of a softer durometer than the tapered tip.

Having thus described embodiments of the present invention and mentioned some significant aspects and features of the present invention, it is the principal object of the present invention to provide a rapid exchange fluid jet thrombectomy device and method of using same to remove thrombus or other unwanted material from a body vessel or other body cavity.

One object of the present invention is to provide a rapid exchange fluid jet thrombectomy device of such size, flexibility and construction as to enable it to pass readily through the tortuous pathways found in the fragile vessels of the heart, the brain, or other body areas, including the more fragile veins.

Another object of the present invention is to provide a rapid exchange fluid jet thrombectomy device with means for producing one or more jets of saline and projecting them in a proximal direction to create a vacuum near the site of thrombus or other unwanted material while pressurizing the exhaust passage.

Yet another object of the present invention is to provide a rapid exchange fluid jet thrombectomy device with outflow orifice means for producing one or more cross stream jets for enhanced removal of thrombus or other unwanted material.

Still another object of the present invention is to provide an improved method of removing thrombus or other unwanted material from an obstructed body vessel.

A further object of the present invention is to provide a smaller diameter rapid exchange fluid jet thrombectomy device wherein the guidewire passes through only a portion of the device resulting in less pressure drop along the exhaust passage, which can also improve the flow of dye through the catheter, thereby increasing catheter performance and procedural performances.

A still further object of the present invention is to provide an efficient, reliable, and less costly method of fabricating a rapid exchange catheter by utilizing an intermediate tube formed with a truncated and rounded slot at a guidewire tube exit region.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
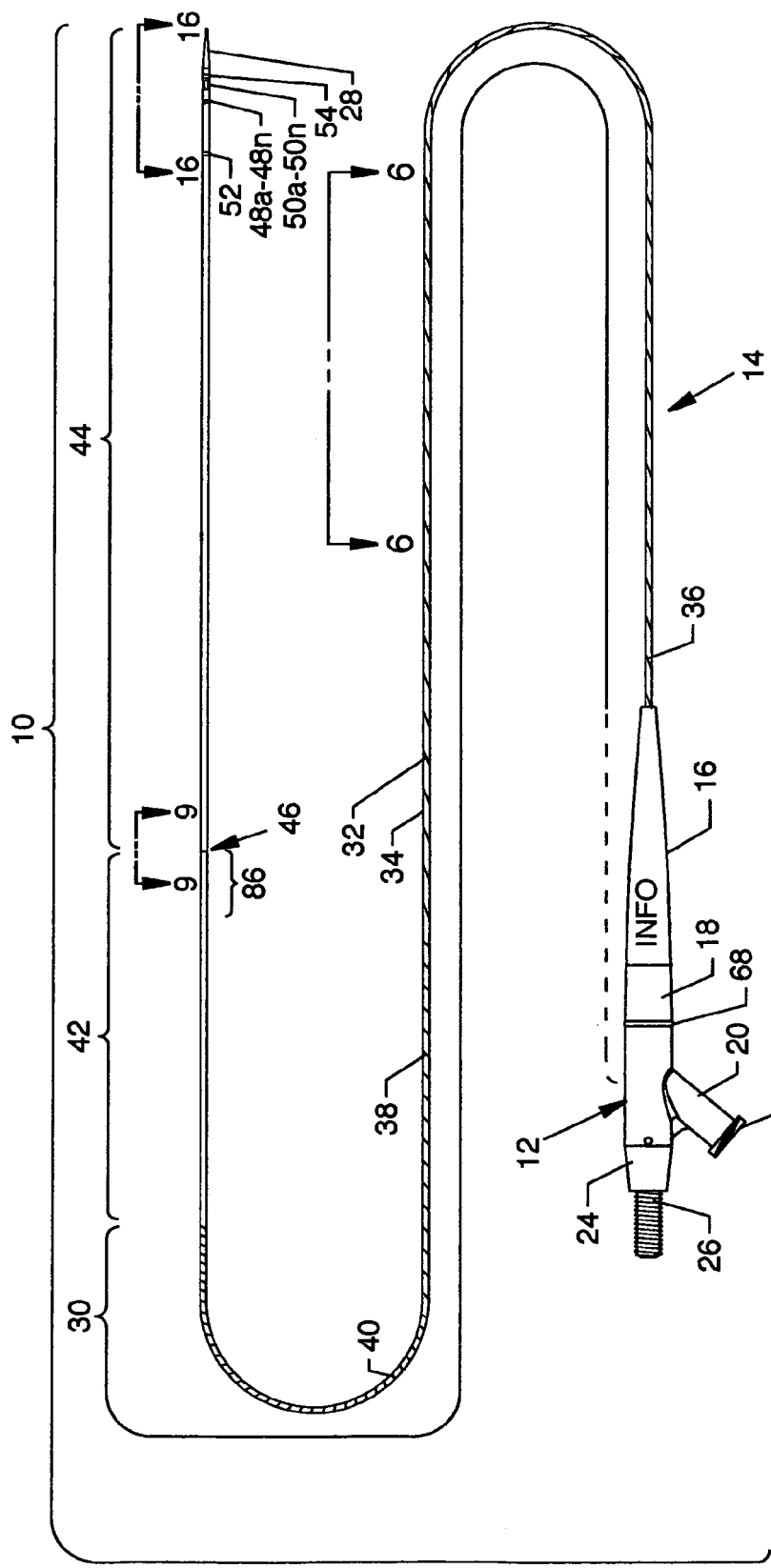
FIG. 1 is a plan view of the readily visible components of a rapid exchange fluid jet thrombectomy device, the present invention, including a manifold with a strain relief and a catheter extending distally from the strain relief.

FIG. 1 is a plan view of the readily visible components of a rapid exchange fluid jet thrombectomy device 10, the present invention, major components of which include a manifold 12 and a catheter 14 extending from the manifold 12. A flexible and tapered strain relief 16 of polymer or other suitable composition connects to and extends distally from the distal portion 18 of the manifold 12 through which the proximal portion of the catheter 14 extends to terminate within the manifold 12. Also included in the structure of the manifold 12 is an exhaust branch 20 having a threaded branch end 22, and a proximal portion 24 which accommodates a threaded high pressure connection port 26.

The catheter 14, an elongated structure, is comprised generally of connected tubular structures of different configurations which terminate at a tapered tip 28, which all function as an exhaust path to exhaust effluent, and which all contain or host various components extending distally from inside the manifold 12 and through the strain relief 16 and terminating at the tapered tip 28. The first tubular structure is a proximal tube 30, the proximal end of which extends through the strain relief 16 to the interior of the manifold 12. The proximal tube 30, which is an assembly, includes a spiral metal tube 32 which can be laser cut or otherwise suitably fashioned. The pitch of the cut can be varied in various schemes along the length of the spiral metal tube 32. The use of the spiral metal tube 32 instead of the easily kinkable, stiff, projecting metal tube of previous designs preserves the excellent pushability and torqueability of previous designs but is less kinkable and more flexible than previous designs. The spiral cut can be transitioned in pitch from distal to proximal to produce a continuous transition from flexible to stiff which maximizes the pushability and "feel" of the catheter 14. The spiral cut along the spiral metal tube 32 can be of many different configurations to achieve the desired property. During manufacturing, the spiral metal tube 32 can be extended or shortened anywhere along the length of the proximal tube 30, or the pitch can be configured to provide a desired mechanical property. A polymer jacket 34, which can be transparent and which can be in the form of a shrink tube, encompasses the spiral metal tube 32, thus creating a leak-free tubular structure as well as adding mechanical and lubricious properties to the catheter 14. For example and for purposes of illustration, various pitches of the spiral metal tube 32, which are constant, can be seen through the polymer jacket 34, if a transparent polymer is incorporated, starting with a wide pitch 36 at the strain relief 16, a medium pitch 38 shown distal to the wide pitch 36, and finally, a close pitch 40 at the distal end of the spiral metal tube 32 where the distal end of the proximal tube 30 is joined to the proximal end of an intermediate tube 42, a second tubular structure. Pitch configurations other than those shown can be incorporated into the proximal tube 30 and can even extend further along the full length of the catheter 14, as described in an alternative embodiment. The intermediate tube 42 provides for overall transition from a distal tube 44, a third tubular structure, to the proximal end of the catheter 14. The proximal end of the intermediate tube 42 attaches over the distal end of the spiral metal tube 32 and polymer jacket 34 by adhesive and/or a heat bond. The intermediate tube 42, preferably of Pebax, can be a material of a harder durometer than the material of the distal tube 44. A guidewire tube exit region 46 is located at the junction of the intermediate tube 42 and the distal tube 44, as later described in detail. Also located near the tapered tip 28 are a plurality of outflow orifices 48a-48n, a plurality of inflow orifices 50a-50n, and radiopaque marker bands 52 and 54.

Figure 2:
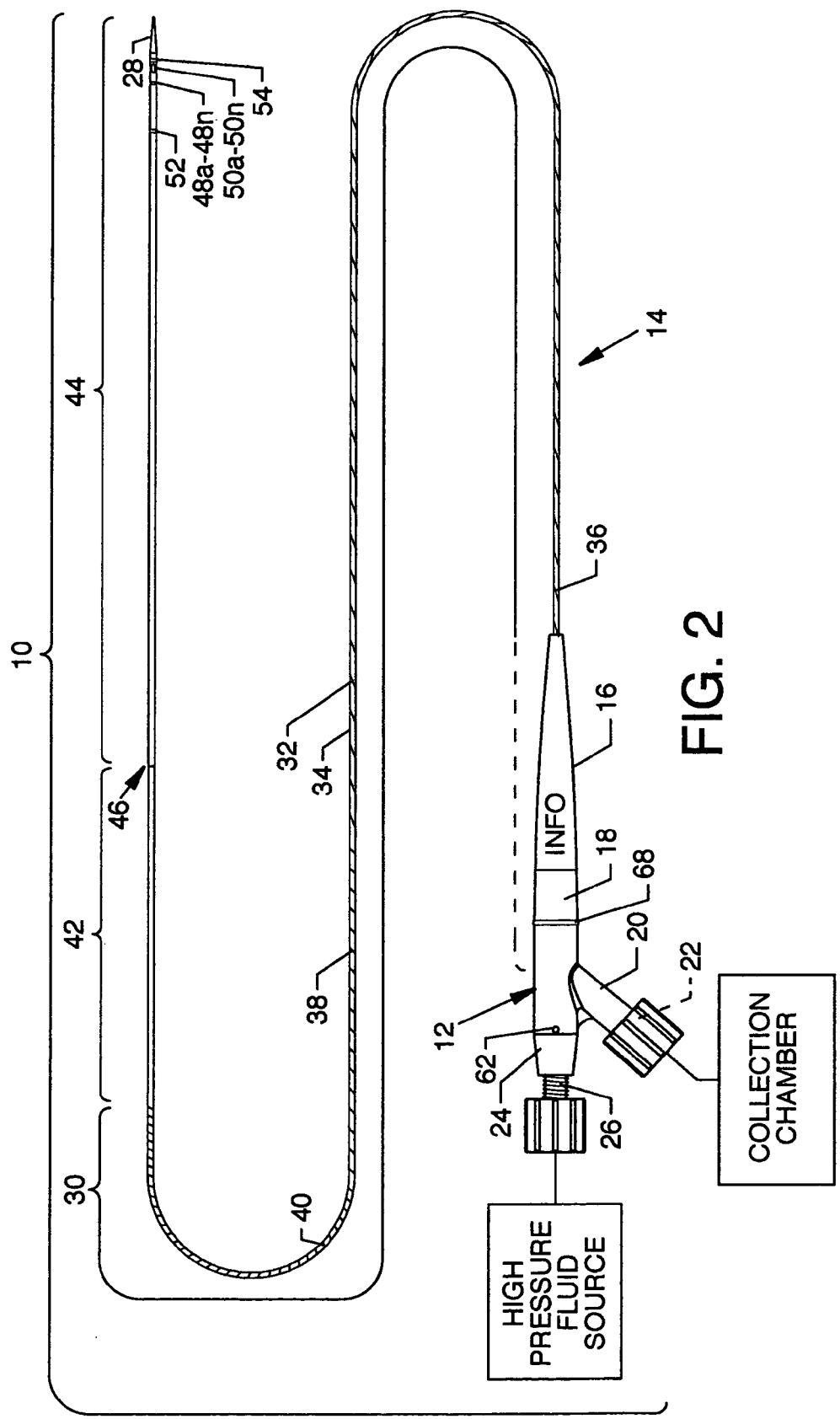
FIG. 2 is a plan view of the rapid exchange fluid jet thrombectomy device indicating high pressure fluid source and collection chamber connections to the manifold.

FIG. 2 is a plan view of the rapid exchange fluid jet thrombectomy device 10 indicating high pressure fluid source and collection chamber connections to the manifold 12.

Figure 3:
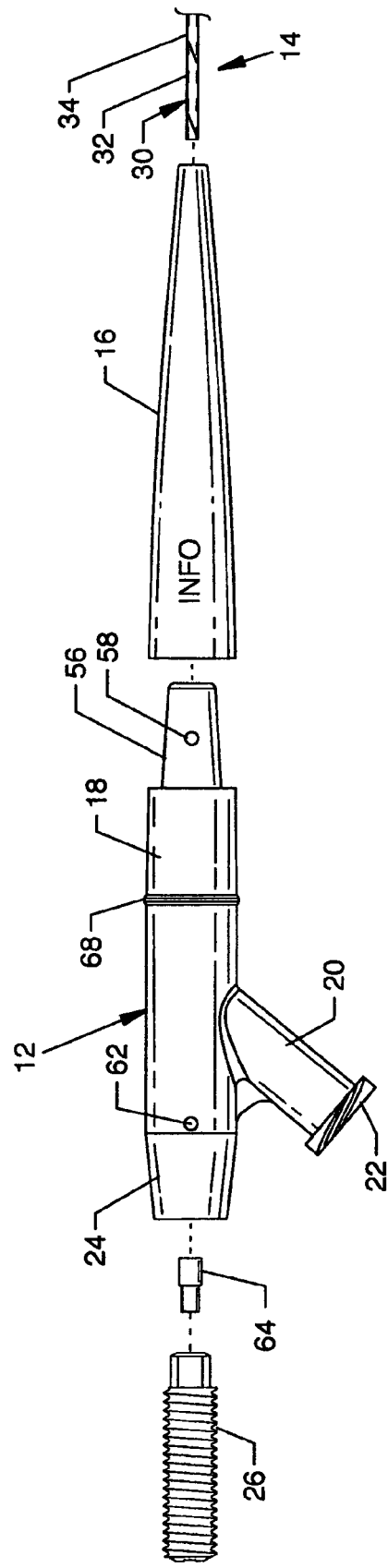
FIG. 3 is an exploded view of the manifold and components mounted to, connected to, or closely associated with the manifold.
Figure 4:
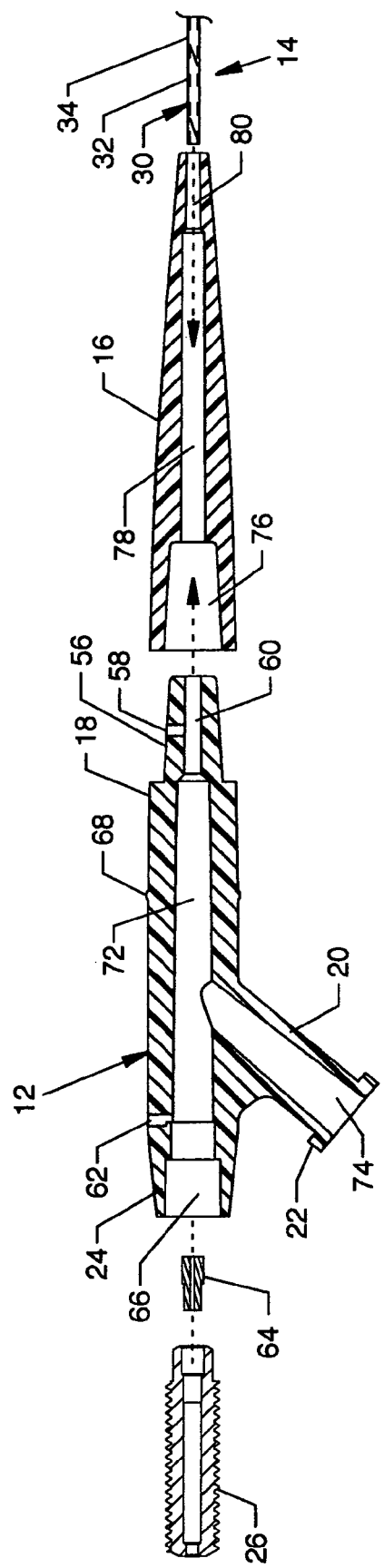
FIG. 4 is an exploded cross section view of the manifold including the components mounted to, connected to, or closely associated therewith.

FIG. 3 is an exploded view of the manifold 12 and components mounted to, connected to, or closely associated with the manifold 12. A tapered extension 56 extends distally at the distal portion 18 of the manifold 12 for accommodation of the strain relief 16. A port 58 (shown in vertical orientation FIG. 4) in the tapered extension 56 is utilized for the introduction of adhesive for securing the proximal region of the proximal tube 30 within a connected bore 60 of the tapered extension 56 (FIG. 4). Introduced adhesive flows within the bore 60 and about the proximal region of the proximal tube 30 and is cured by ultraviolet light for mutual bonding. Another port 62 (shown in vertical orientation FIG. 4) at the proximal portion 24 of the manifold 12 is utilized for the introduction of adhesive for securing the threaded high pressure connection port 26 and a co-located ferrule 64 within a connected multi-radius receptor bore 66 in the proximal portion 24 of the manifold 12 (FIG. 4). Introduced adhesive flows within the proximal portion of a central passageway 72 within manifold 12 (FIG. 4), within the adjoining distal portion of the multi-radius receptor bore 66 and against the distal portions of the threaded high pressure connection port 26 and the ferrule 64, and about the proximal region of a high pressure tube 70 (FIG. 5), and is cured by ultraviolet light for mutual bonding. A ring 68 extends about the manifold 12 for use with a catheter end securing clip (not shown).

Figure 5:
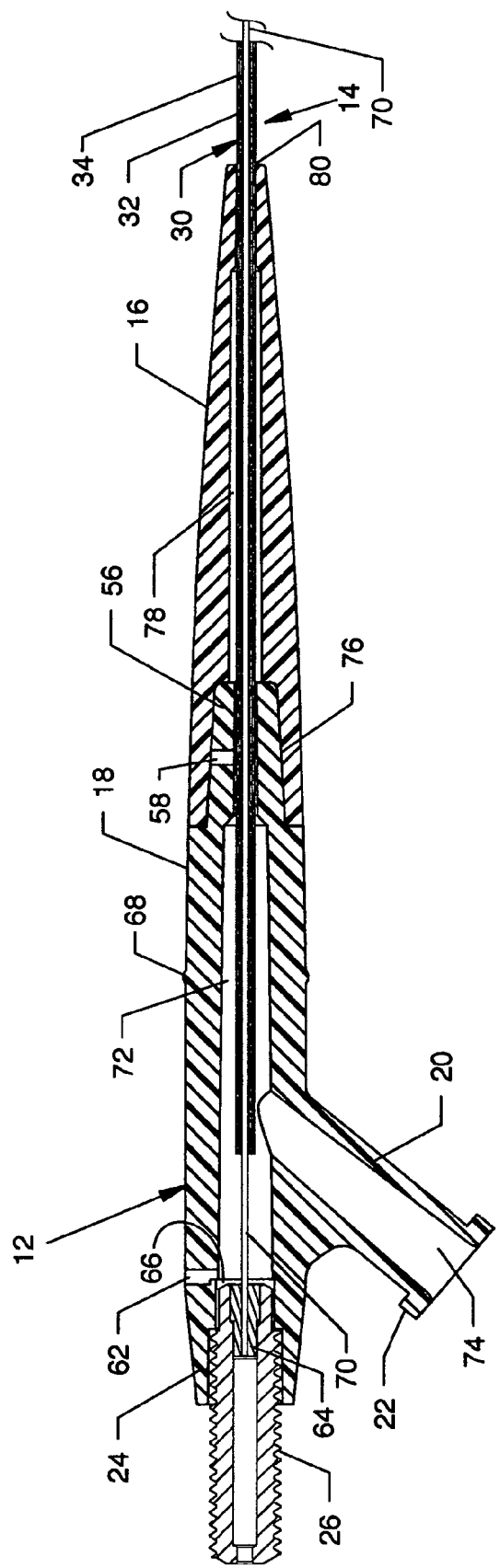
FIG. 5 is a cross section view of the components of FIG. 4 assembled and including a high pressure tube.

FIG. 4 is an exploded cross section view of the manifold 12 including the components mounted to, connected to, or closely associated therewith; and FIG. 5 is a cross section view of the components of FIG. 4 assembled and including the high pressure tube 70. With reference to FIGS. 4 and 5, the manifold 12 including the components mounted to, connected to, or closely associated therewith is further described. Central to the manifold 12 is the central passageway 72 located between the multi-radius receptor bore 66 and the opposed distally located bore 60. An exhaust branch passageway 74 aligned within the exhaust branch 20 intersects and communicates with the central passageway 72 and also communicates with the lumen 82 of the proximal tube 30. It is to be noted that the high pressure tube 70 is also located within the lumen 82 of the proximal tube 30 (as more clearly seen in FIG. 6) and extends distally along the connected lumens of the intermediate tube 42 and the distal tube 44. High pressure tube 70 is secured at its proximal end to the threaded high pressure connection port 26 by use of the ferrule 64. The strain relief 16 includes connected cavities and passages aligned along and about the longitudinal axis thereof. The proximal portion of the strain relief 16 includes a tapered cavity 76 connected to the proximal end of a centrally located passageway 78 and a distally located passageway 80 connected to the distal end of the centrally located passageway 78. The tapered cavity 76 is correspondingly shaped for accommodation by the tapered extension 56 and can be secured thereto such as by adhesive. The strain relief 16 provides much more adequate strain relief due to the gradual tapered design. In addition to this, verbiage specifying mode of operation, French size, or other information can be pad printed on the strain relief 16 (as indicated by the term "INFO" in FIGS. 1-3) instead of being molded directly therein, thereby greatly improving the visibility of the information for the benefit of medical personnel.

Figure 6:
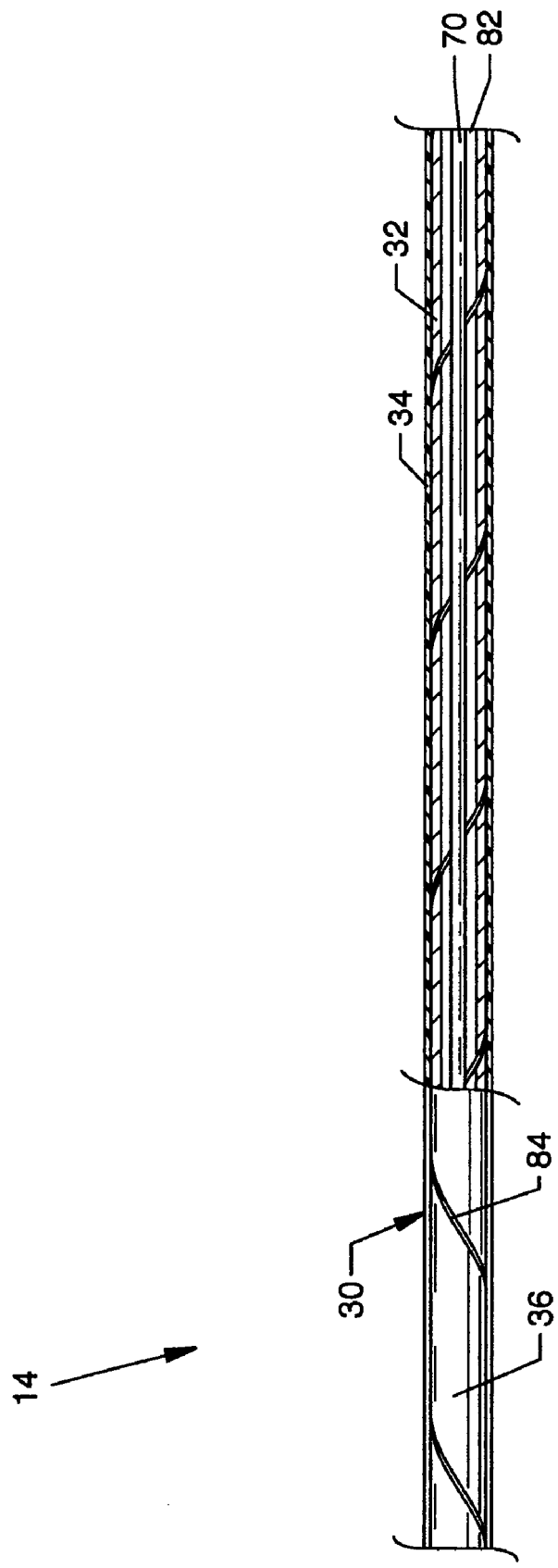
FIG. 6 is a partial cross section view of the catheter along line 6-6 of FIG. 1.

FIG. 6 is a partial cross section view of the catheter 14 along line 6-6 of FIG. 1. Provided that the polymer jacket 34 material encasing the spiral metal tube 32 is transparent, the spiral metal tube 32 is easily viewed therethrough. A spiral cut 84 extends along and about the spiral metal tube 32, and the polymer jacket 34 is closely aligned over and about the spiral metal tube 32. The spiral cut 84 can be produced by a laser cutting tool, or other suitable fashioning methods can be incorporated to produce a continuous spiral metal tube 32 which can include several spiral pitch configurations. One configuration is shown in FIG. 1, in which, for purposes of example and illustration, there are adjacent continuous sections of constant pitch where one pitch is a wide pitch 36, the next pitch is a medium pitch 38, and the last pitch is a close pitch 40. Another configuration could be one in which a spiral metal tube extends the full length of the catheter 14, instead of just along the length of the proximal tube 30, to a point short of the outflow orifices 48a-48n. In another configuration the spiral metal tube could extend distally beyond the inflow orifices 50a-50n to the flexible tip 28. A still further configuration could be one in which the pitch decreases progressively along the partial length or full length of the catheter 14. Clearly, many configurations can be incorporated to achieve required pushability and torqueability to meet different criteria.

Figure 7:
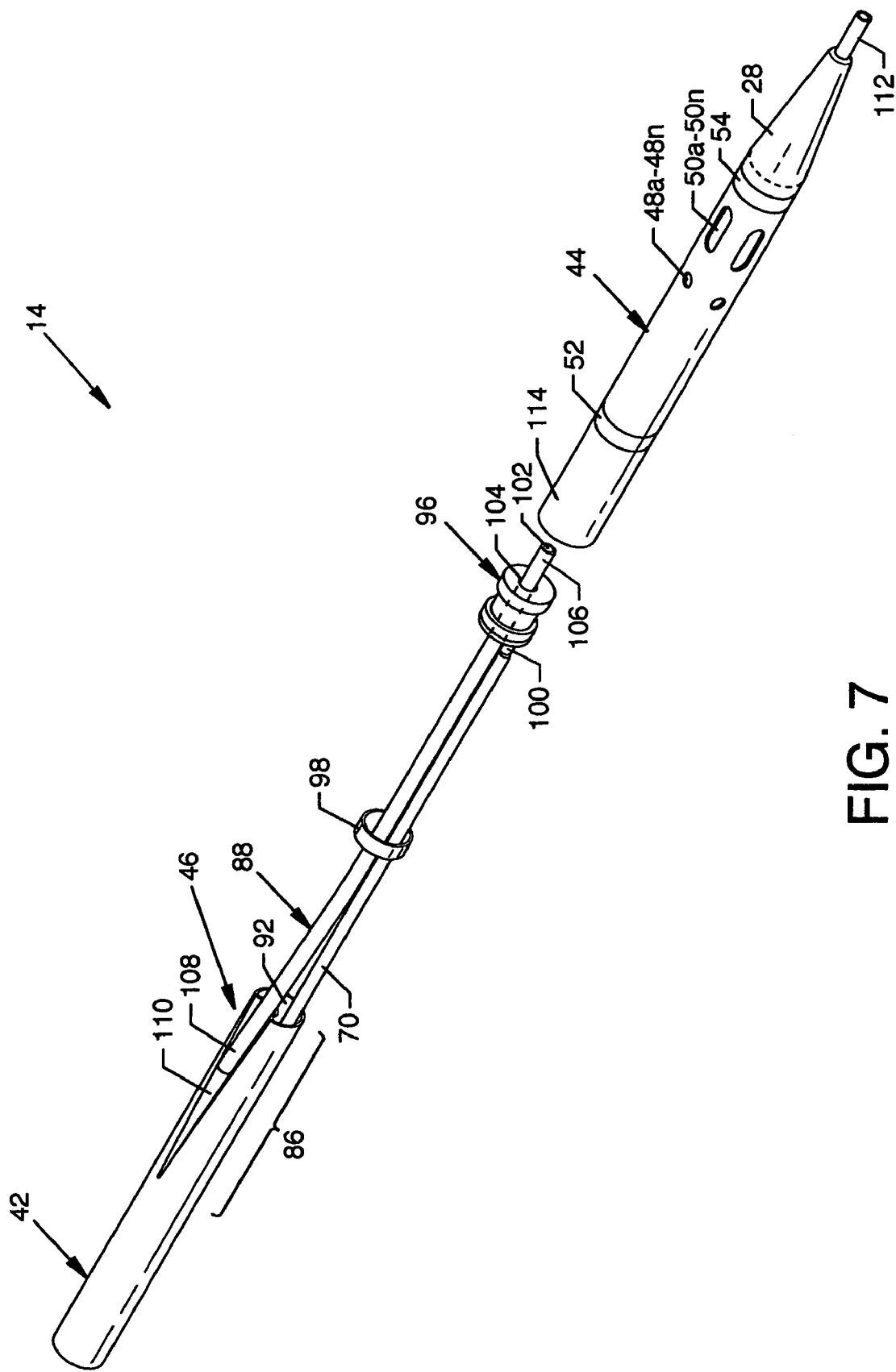
FIG. 7 is an exploded and separated isometric view of the components of the catheter from and including a distally located formed tubular portion of the intermediate tube to the tapered tip of the distal tube, some components being foreshortened with respect to length for the purpose of illustration and clarity.

FIG. 7 is an exploded and separated isometric view of the components of the catheter 14 from and including a distally located formed tubular portion 86 of the intermediate tube 42 to the tapered tip 28 of the distal tube 44, some components being foreshortened with respect to length for the purpose of illustration and clarity. The shown portion of the catheter 14 includes the intermediate tube 42, a flexible guidewire tube 88 of polymer, the high pressure tube 70, a fluid jet emanator 96, the distal tube 44, and other components within, along, and about the catheter 14.

Figure 16:
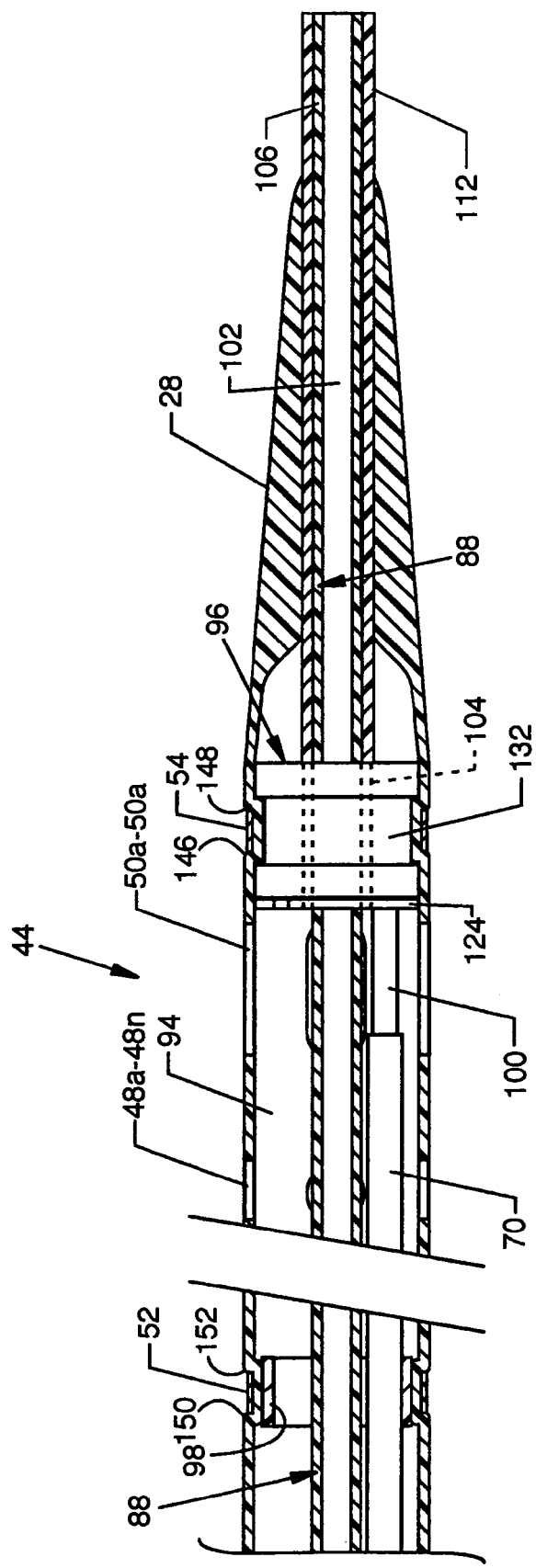
FIG. 16 is a cross section view of the distal portion of the distal tube including the tapered tip and showing internal components along line 16-16 of FIG. 1.

The high pressure tube 70 with a lumen 90 (FIG. 9) extends from the manifold 12, as previously described, through the lumen 82 in the proximal tube 30, through a lumen 92 in the intermediate tube 42, and through a lumen 94 (FIG. 16) of the distal tube 44 and connectively terminates at the fluid jet emanator 96. The high pressure tube 70 also extends through and is attached to a tube support ring 98 such as by welding or other suitable means. The fluid jet emanator 96, as well as the distal end 100 of the high pressure tube 70, locate distally in the lumen 94 of the distal tube 44, as shown in FIG. 16. The radiopaque marker band 54 aligns over and about the distal region of the distal tube 44 and is forcibly secured thereto in captured alignment and in transmitted frictional engagement with the fluid jet emanator 96, as shown in FIG. 16. The tube support ring 98 locates in lumen 94 of the distal tube 44 in alignment with the radiopaque marker band 52 which forcibly secures over and about the distal tube 44 in transmitted frictional engagement, as shown in FIG. 16. The guidewire tube 88, having a lumen 102, extends distally from the guidewire tube exit region 46 through the lumen 94 of the distal tube 44 and through the tube support ring 98, through a passageway 104 in the fluid jet emanator 96, and further through the lumen 94 of the distal tube 44 to where the distal portion 106 terminates securely, such as by heat bonding or other suitable means, within a soft tip extension tube 112 (FIG. 16) which is flexible and which is located in and extends distally beyond the general body of the tapered tip 28. Heat can be applied to form the tapered tip 28 of increasingly flexible shape, in a distal direction, at the end of the distal tube 44, as well as to engagingly secure the distal end portion 106 of the guidewire tube 88 to and within the tip extension tube 112 of the tapered tip 28. The tapered tip 28 may also be formed through a cold draw-down process or may be physically attached through adhesives or polymer reintegration. The proximal end 108 of the guidewire tube 88 is securely accommodated by a crescent-shaped truncated and rounded slot 110 at the distally located formed tubular portion 86 of the intermediate tube 42 described with reference to FIG. 8. The plurality of outflow orifices 48a-48n and the plurality of inflow orifices 50a-50n spaced distal to the outflow orifices 48a-48n are included around and about the distal region of the distal tube 44.

Figure 8:
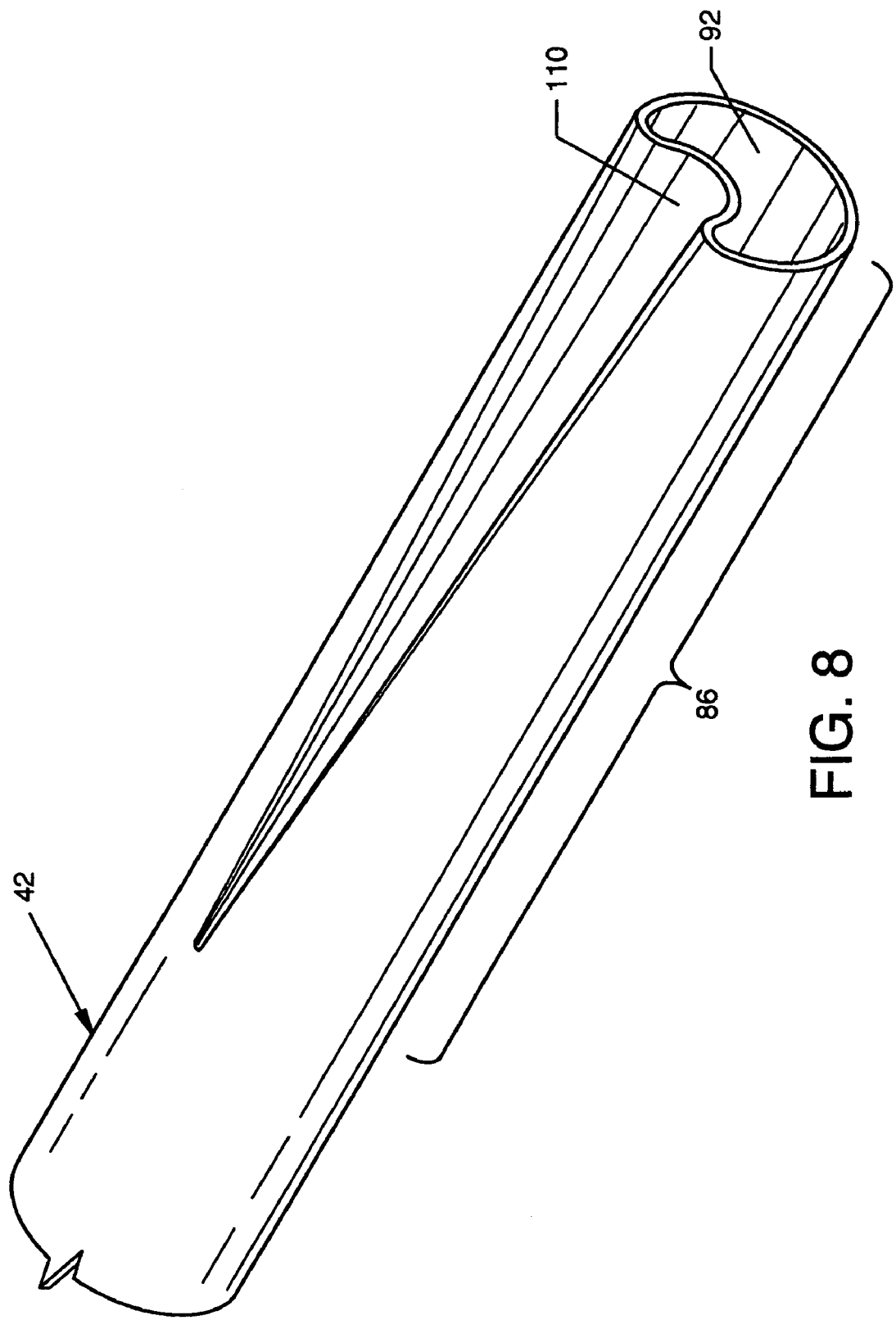
FIG. 8 is an isometric view of the distally located formed tubular portion of the intermediate tube.
Figure 9:
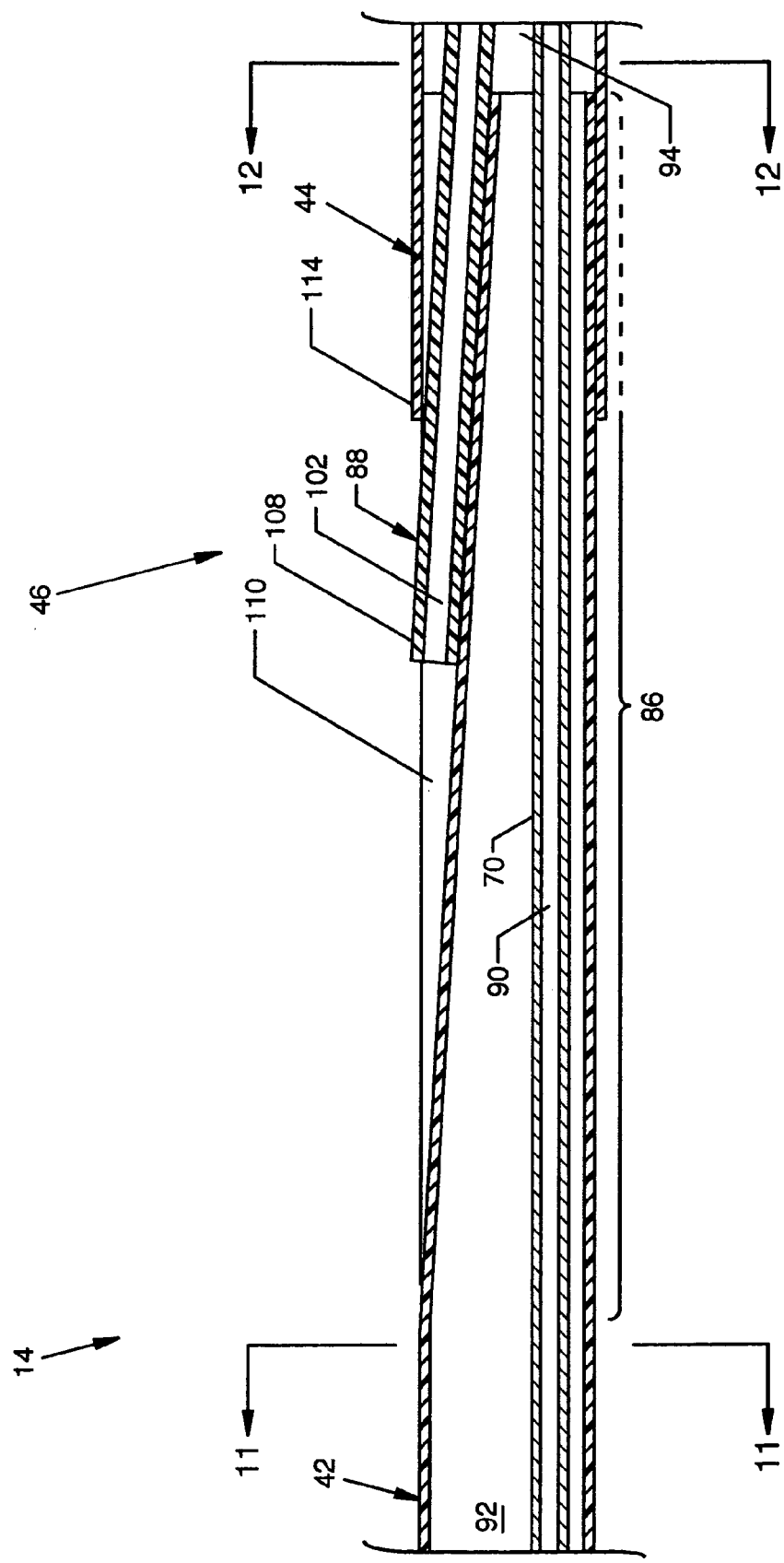
FIG. 9 is a cross section view of the catheter along line 9-9 of FIG. 1.

FIG. 8 is an isometric view of the distally located formed tubular portion 86 of the intermediate tube 42 which can be formed, molded, machined, extruded or otherwise fashioned of plastic or other suitable material. The distally located formed tubular portion 86 includes geometry in the form of a truncated and rounded slot 110 of decreasing depth, in a proximal direction, which accommodates the proximal end 108 of the guidewire tube 88 (FIG. 7). The truncated and rounded slot 110 is substantially formed in the shape of a nearly full semi-circular arc at the extreme distal end of the distally located formed tubular portion 86. The arc, while the radius remains constant, is decreased progressing proximally from the extreme distal end of the distally located formed tubular portion 86 to provide for angled transitional accommodation of the guidewire tube 88, as shown in FIGS. 7 and 9. Lumen 92 interior to the intermediate tube 42 accommodates the high pressure tube 70 and also functions as part of the overall effluent exhaust path formed with connected lumens 82 and 94.

FIG. 9 is a cross section view of the catheter 14 along line 9-9 of FIG. 1. Shown in particular is the distally located formed tubular portion 86 of the intermediate tube 42 in intimate low profile engagement with the proximal end 114 of the distal tube 44 and with the proximal end 108 of the guidewire tube 88 at the guidewire tube exit region 46. Adhesives, welding, thermal bonding, heat shrinking, or other such suitable methods involving or not involving heat-generated bonding, can be incorporated to bond the distally located formed tubular portion 86 of the intermediate tube 42 with the proximal end 114 of the distal tube 44. The proximal end 108 of the guidewire tube 88 is accommodated by the truncated and rounded slot 110 of the intermediate tube 42 and is secured thereto by an adhesive, by welding or other such suitable method. The proximal end 108 of the guidewire tube 88 is of such length that the outer profile of the distal tube 44 or the outer profile of the intermediate tube 42 is not exceeded to maintain the desired minimal catheter profile. The portion of the truncated and rounded slot 110 which is not occupied by the proximal end 108 of the guidewire tube 88 and which is proximal thereto can also be utilized to accommodate a guidewire without structure interference. Also illustrated is the high pressure tube 70, having the lumen 90, passing through the lumens 92 and 94. Lumen 82 of the proximal tube 30, lumen 92 of the intermediate tube 42, and lumen 94 of the distal tube 44 are connected to function as an exhaust route extending the length of the catheter 14.

Figure 10:
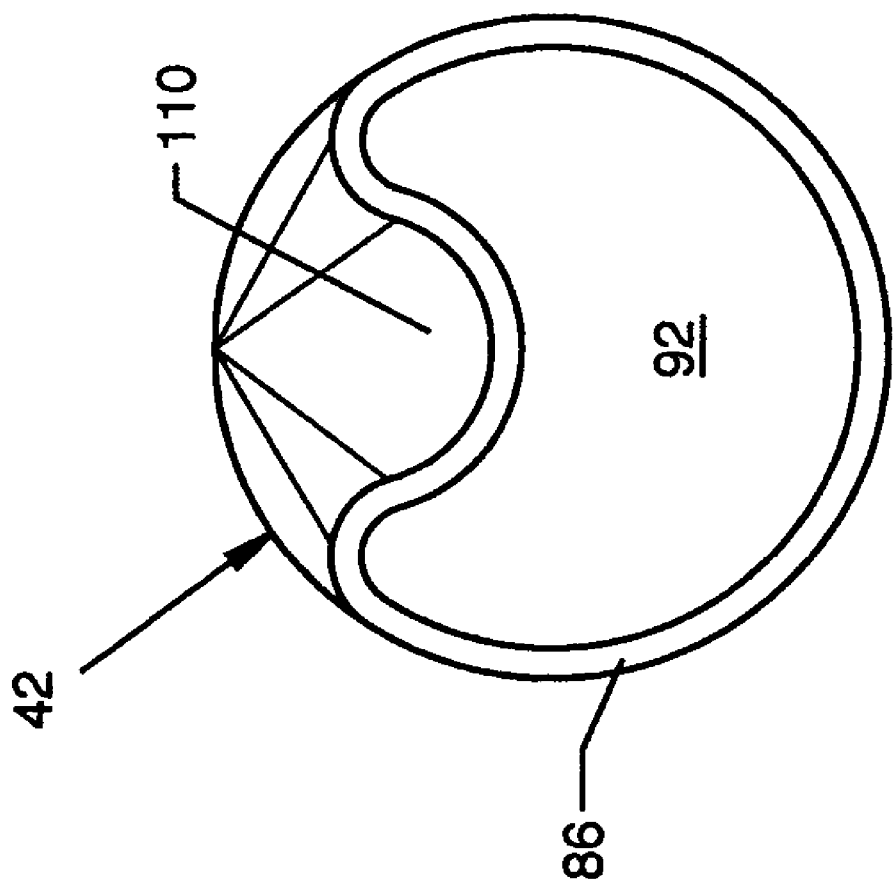
FIG. 10 is an end view of the distally located formed tubular portion of the intermediate tube.

FIG. 10 is an end view of the distally located formed tubular portion 86 of the intermediate tube 42. Illustrated in particular is the extreme distal end of the truncated and rounded slot 110 having a maximum arc.

Figure 11:
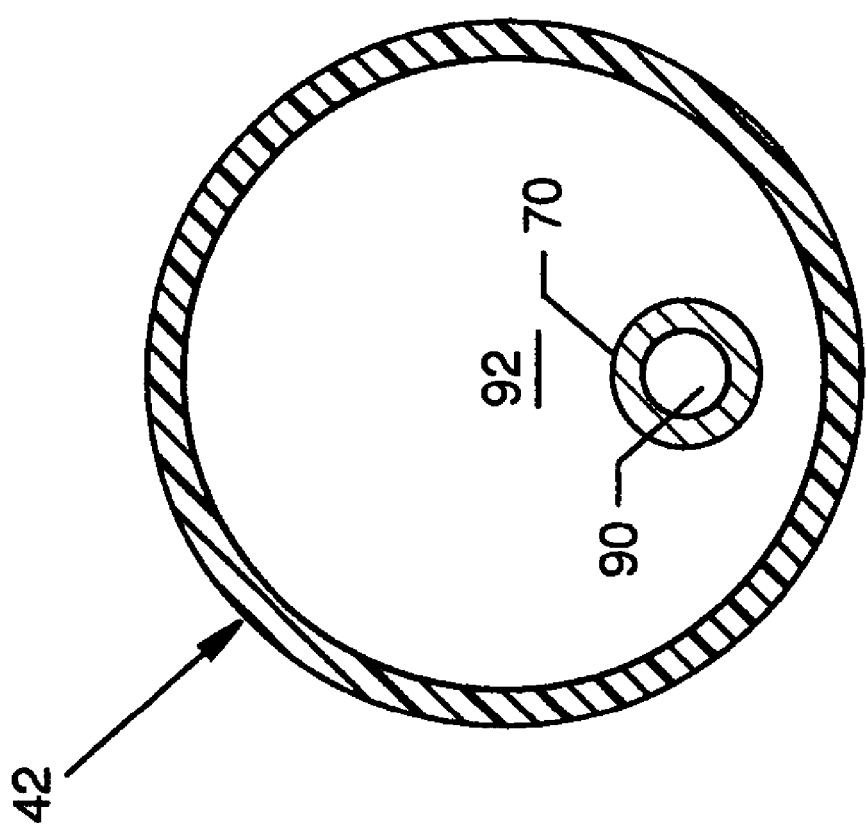
FIG. 11 is a cross section view along line 11-11 of FIG. 9.

FIG. 11 is a cross section view along line 11-11 of FIG. 9. Illustrated in particular is the lumen 92 of the intermediate tube 42 which functions as an exhaust route with minimal obstructions or restrictions therein.

Figure 12:
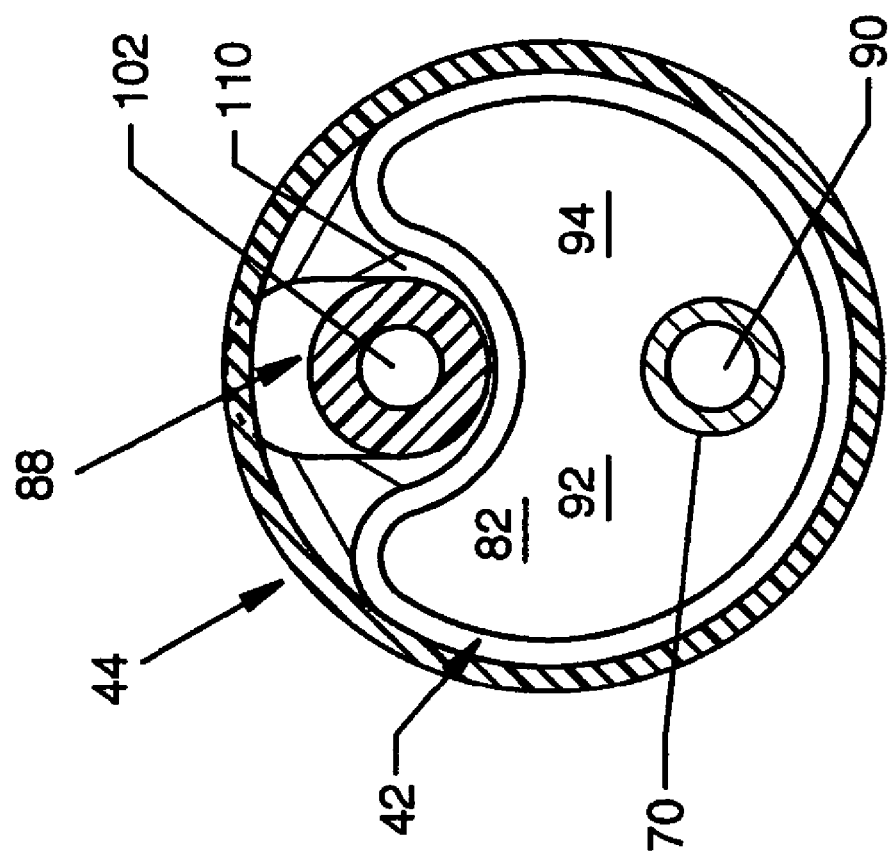
FIG. 12 is a cross section view along line 12-12 of FIG. 9.

FIG. 12 is a cross section view along line 12-12 of FIG. 9. Illustrated in particular is the alignment and accommodation of the guidewire tube 88 in the truncated and rounded slot 110 at the distally located formed tubular portion 86 of the intermediate tube 42. Also illustrated are the lumens 82, 92 and 94 in alignment to function as an exhaust route through the catheter 14.

Figure 13:
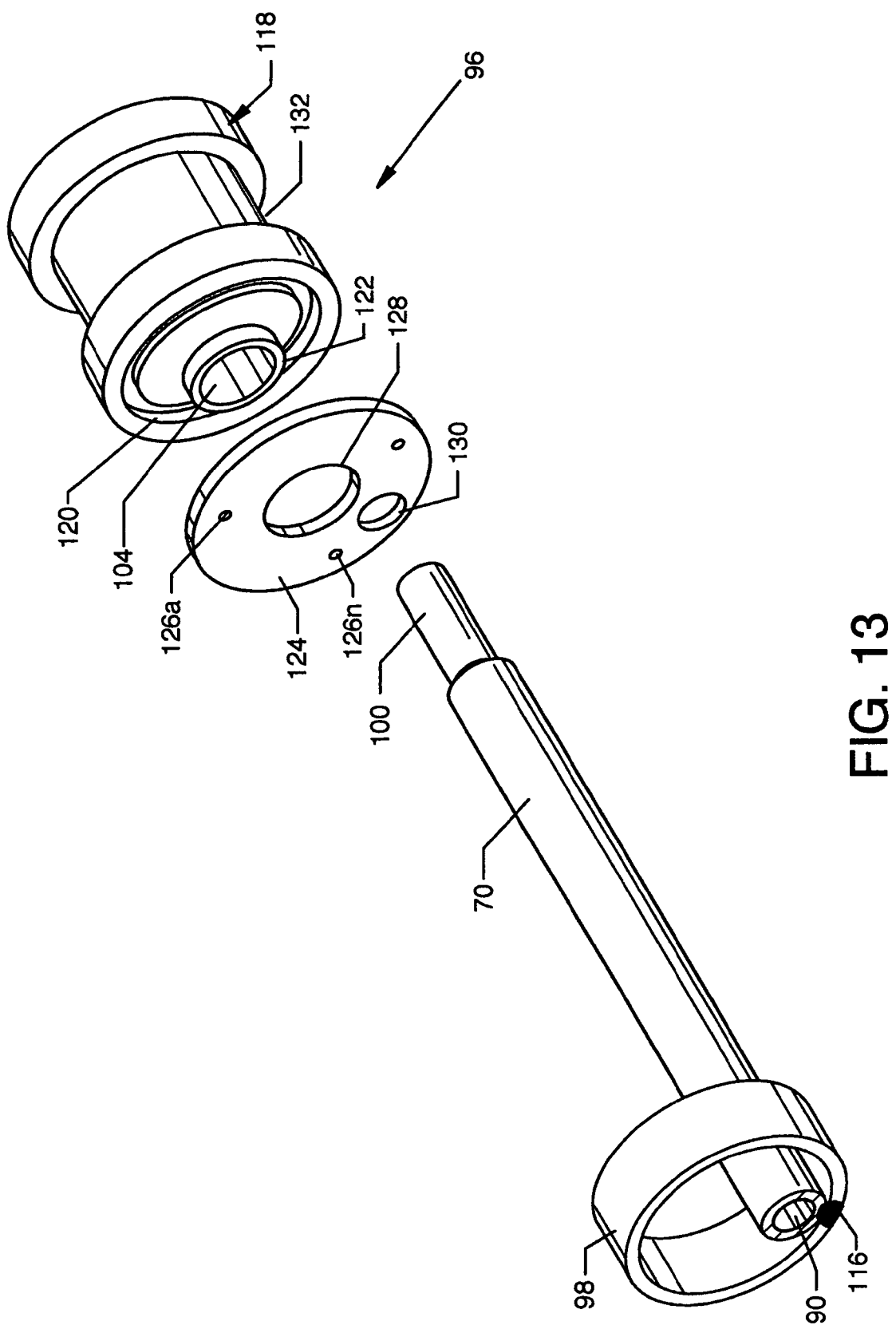
FIG. 13 is an exploded isometric view depicting the relationship of the fluid jet emanator, the tube support ring, and the high pressure tube to one another.

FIG. 13 is an exploded isometric view depicting the fluid jet emanator 96, the tube support ring 98, and the high pressure tube 70 in relationship to one another. The tube support ring 98 secures such as by a weld 116 or other suitable attachment method to the lower surface of the high pressure tube 70, thereby fixing the tube support ring 98 at a suitable position along the interior (lumen 94) of the distal tube 44 for engagement with the distal tube 44 by compressional frictional engagement of the radiopaque marker band 52 over and about the distal tube 44 and co-located tube support ring 98.

Figure 14:
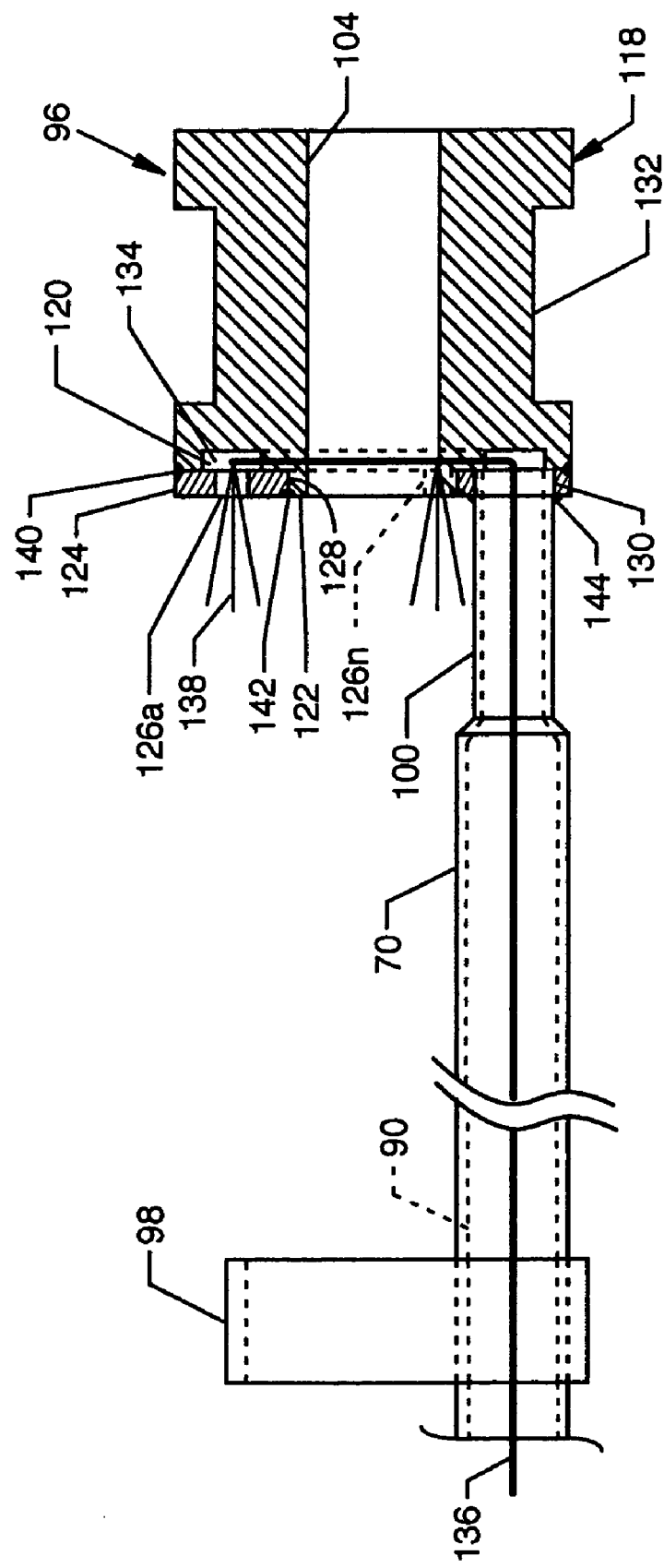
FIG. 14 is a side view in partial cross section of the components illustrated in FIG. 13 assembled.

The high pressure tube 70 is reduced in diameter at the high pressure tube distal end 100 to engage the fluid jet emanator 96. The fluid jet emanator 96 is described with reference to FIGS. 13, 14 and 15. The fluid jet emanator 96 is built as a structure outwardly resembling the general shape of a spool. The fluid jet emanator 96 includes a cylindrical main body 118, an annular manifold groove 120 in the form of a circular groove at the proximal end of the cylindrical main body 118, a centrally located tubular extension 122 extending proximally from the proximal end of the main body 118 and being coaxial with the annular manifold groove 120, and a manifold plate 124 aligned to the annular manifold groove 120 and to the planar annular surfaces adjacent to the annular manifold groove 120 and having a plurality of jet orifices 126a-126n, a centrally located hole 128, and an offset hole 130. The centrally located hole 128 is aligned to and accommodated by the tubular extension 122. The manifold plate 124 is also aligned substantially to the distal end of the main body 118 during the mating of the centrally located hole 128 and the tubular extension 122. The passageway 104 aligns to the longitudinal axis of the main body 118, the center of the tubular extension 122, and the center of the hole 128 of the manifold plate 124. An annular groove 132 is formed about the main body 118. As shown in FIG. 14, an annular manifold 134 is formed when the manifold plate 124 is mated over and about the annular manifold groove 120 and adjacent planar annular surfaces of the fluid jet emanator 96 at which time the plurality of jet orifices 126a-126n and the offset hole 130 are brought into close communicational alignment with the annular manifold groove 120 and annular manifold 134.

High pressure fluid 136 (FIG. 14) such as saline or other suitable solution is delivered through the lumen 90 of the high pressure tube 70 to the fluid jet emanator 96 and distributed through the annular manifold 134 to the plurality of jet orifices 126a-126n whereby high velocity fluid jet flow 138 emanates proximally, as described later in detail.

The radiopaque marker band 54 and the annular groove 132 in the main body 118 of the fluid jet emanator 96 are utilized to fix the fluid jet emanator 96 and associated components and structures at the proper position within the distal end of the distal tube 44, as illustrated in FIG. 16. The radiopaque marker band 54 positions over and about the distal end of the distal tube 44 for engagement with the distal tube 44 by compressional frictional engagement of the radiopaque marker band 54 over and about distal tube 44 in the co-located region of the annular groove 132 and the distal tube 44.

FIG. 14 is a side view in partial cross section of the components illustrated in FIG. 13 assembled. Illustrated in particular is the connective relationship of the lumen 90 of the high pressure tube 70 to the annular manifold 134. High pressure fluid 136 is delivered to the annular manifold 134 through the lumen 90 and is emanated outwardly and proximally through the jet orifices 126a-126n in the form of high velocity fluid jet flow 138 in multiple jet streams. Integrity of the annular manifold 134 is ensured by an annular weld 140 joining the common mated peripheries of the manifold plate 124 and adjacent main body 118 of the fluid jet emanator 96 and by another annular weld 142 joining the junction of the tubular extension 122 and the manifold plate 124. An annular weld 144 securingly seals the distal end 100 of the high pressure tube 70 within the offset hole 130, thereby ensuring the integrity of the connection of the lumen 90 with the annular manifold 134.

Figure 15:
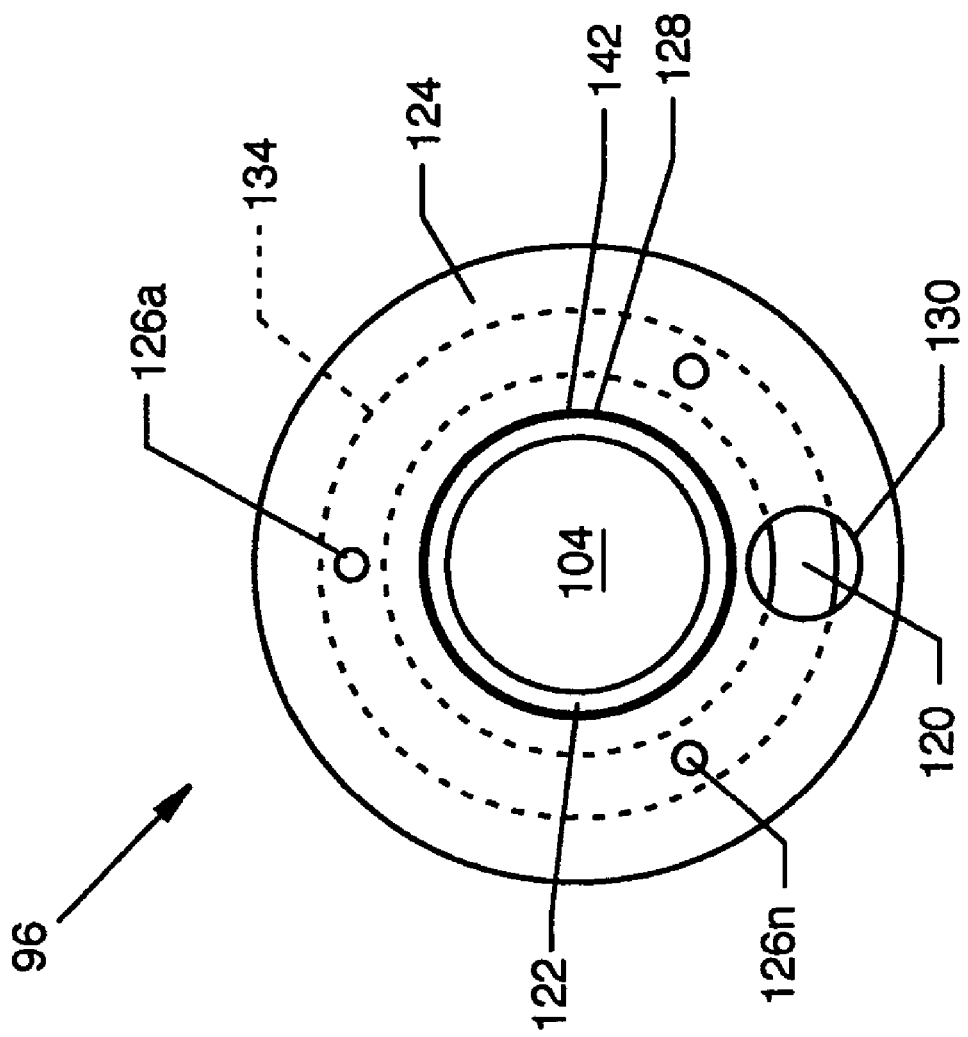
FIG. 15 is a proximal end view of the fluid jet emanator.

FIG. 15 is a proximal end view of the fluid jet emanator 96. Illustrated in particular is the distribution and alignment of the jet orifices 126a-126n about the annular manifold 134 through which high velocity fluid jet flow 138 emanates proximally.

FIG. 16 is a cross section view of the distal portion of the distal tube 44 including the tapered tip 28 and showing internal components along line 16-16 of FIG. 1. Shown in the illustration is the positioning of the radiopaque marker bands 52 and 54 around and about the distal portion of the distal tube 44. The distally located radiopaque marker band 54 is forcibly applied over and about the distal tube 44 to cause frictional annular engagement of a portion of the distal tube 44 with all or part of the annular groove 132 of the fluid jet emanator 96. Such frictional engagement is sufficient to place the outer radius surface of the radiopaque marker band 54 in a position lesser than the general and greater outer radial surface of the distal tube 44, thereby providing in part a distal tube 44 having no elements protruding beyond the general outer radial surface thereof for unimpeded and smooth distal or proximal transition of the catheter 14 within a vein, artery or the like. The frictional engagement of the radiopaque marker band 54 over and about the distal tube 44 is not abrupt in nature with respect to the smooth surface of the distal tube 44 wherein opposed curved annular surfaces 146 and 148 are formed adjacent to the edges of the radiopaque marker band 54. The curved annular surfaces 146 and 148 are generally smooth in nature and thereby aid in unimpeded and smooth distal or proximal transition of the catheter 14 within a vein, artery or the like. The proximally located radiopaque marker band 52 is also forcibly applied over and about the distal tube 44 to cause frictional annular engagement of a portion of the distal tube 44 with the tube support ring 98, much in the same manner as the radiopaque marker band 54. Such frictional engagement is sufficient to place the outer radius surface of the radiopaque marker band 52 in a position lesser than the general and greater outer radial surface of the distal tube 44, thereby providing in part a distal tube 44 having no elements protruding beyond the general outer radial surface thereof for unimpeded and smooth distal or proximal transition of the catheter 14 within a vein, artery or the like. The curved annular surfaces 150 and 152 are generally smooth in nature and thereby aid in unimpeded and smooth distal or proximal transition of the catheter 14.

Structure is provided to nurture and aid introduction of and passage of the distal portion of the distal tube 44 through blood vessels to the sites of thrombotic deposits or lesions. The tapered tip 28, as opposed to a rounded but nontapered tip, can part and more easily penetrate thrombotic deposits or lesions during insertional travel in a distal direction instead of advancing or pushing such thrombotic deposits or lesions distally. The decreasing diameter in a distal direction of the tapered tip 28 also allows for increasing flexibility to negotiate and pass through tortuous paths. The portion of the distal tube 44 which immediately follows the tapered tip 28 on a tortuous negotiation and passage is influenced by supportive structure which offers reinforcement of the distal tube 44 against bending or collapsing due to negative pressures, especially in the regions in close proximity to or including the inflow orifices 50a-50n and the outflow orifices 48a-48n. The tube support ring 98 and the fluid jet emanator 96 are examples of structures offering support or reinforcement along the distal tube 44 in the regions of the inflow and outflow orifices 50a-50n and 48a-48n, respectively. The tube support ring 98 and the fluid jet emanator 96 also serve as forms and contribute to maintaining the diameter of the distal tube 44. Such support allows the use of thinner wall dimension for the distal tube 44 to allow for a larger and more effective and efficiently sized lumen 94, as well as contributing to a lesser sized outer diameter. Such support also contributes to supportively maintaining the diameter and overall shape of the distal tube 44 when the catheter 14 is pushed or advanced along a vein or other vessel, as well as provides torsional support.

Mode of Operation

Figure 17:
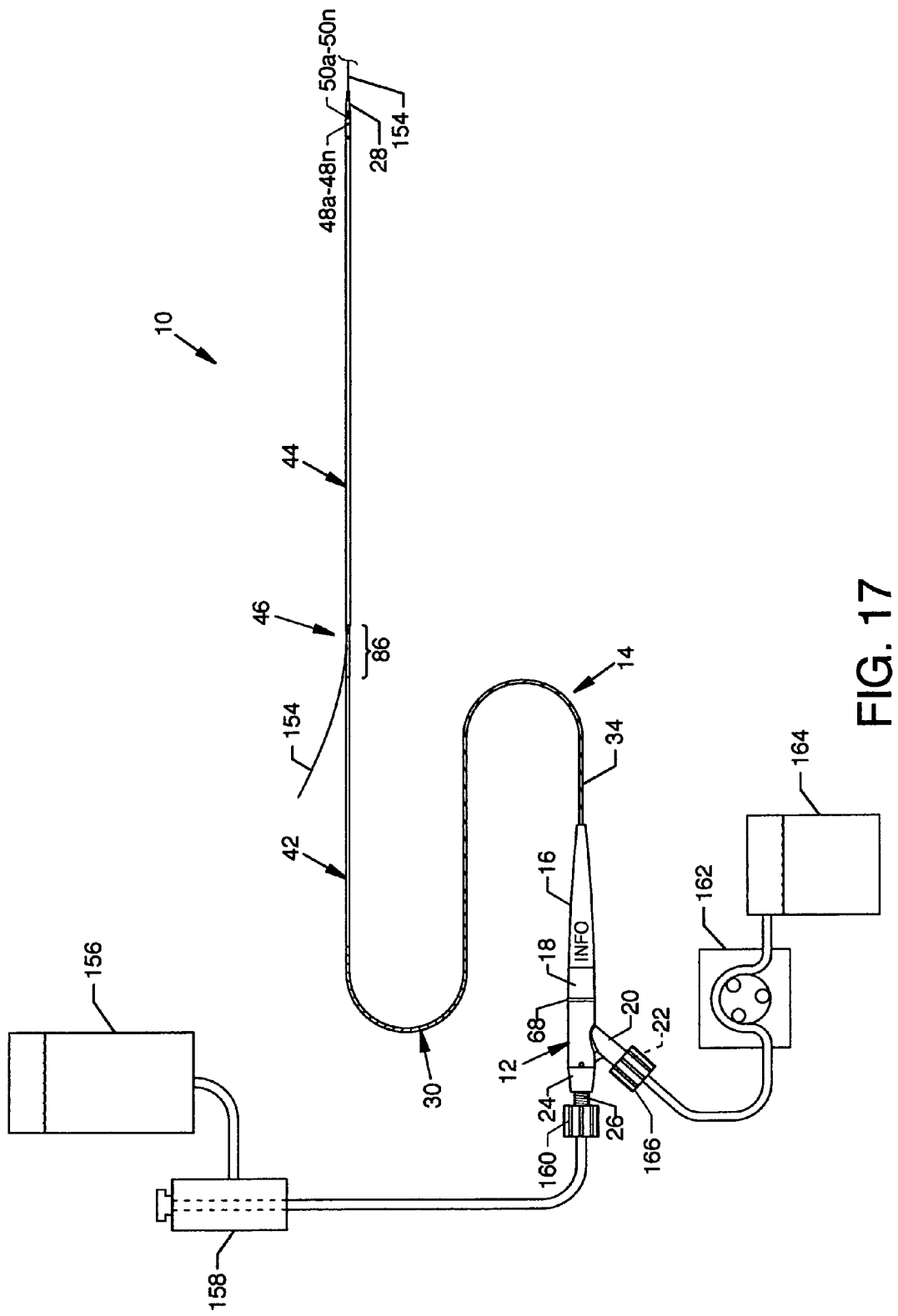
FIG. 17 is a view illustrating the mode of operation where the rapid exchange fluid jet thrombectomy device is connected to ancillary devices.
Figure 18:
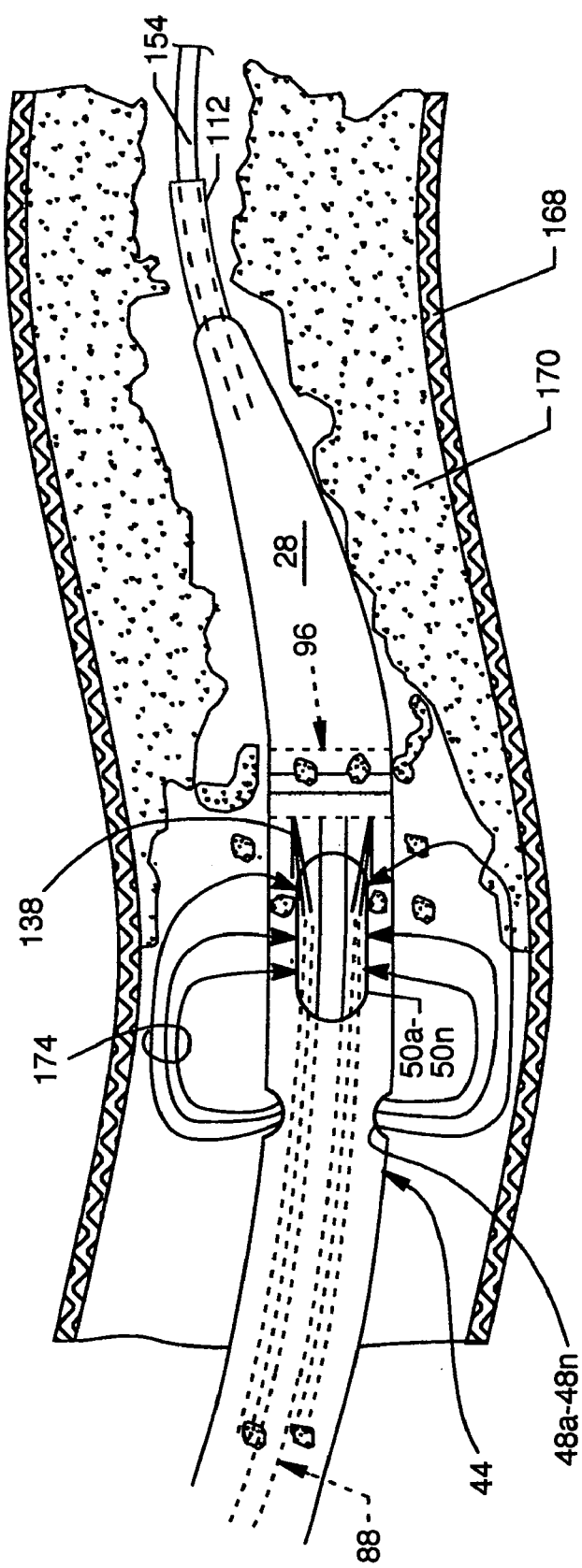
FIG. 18 is a side view of the distal region of the rapid exchange fluid jet thrombectomy device in the performance of the method of use thereof within a blood vessel (shown in cross section) at a site of a thrombotic deposit or lesion.

FIGS. 17 and 18 illustrate the mode of operation where FIG. 17 illustrates the rapid exchange fluid jet thrombectomy device 10 connected to ancillary devices, and where FIG. 18 illustrates a side view of the distal region of the rapid exchange fluid jet thrombectomy device 10 in the performance of the method of use thereof within a blood vessel 168 (shown in cross section) at a site of a thrombotic deposit or lesion 170. The mode of operation is best understood by referring to the FIGS. 17 and 18, as well as previously described figures.

In FIG. 17 the rapid exchange fluid jet thrombectomy device 10 is shown engaged over and about a guidewire 154 where the guidewire 154 (previously engaged in the blood vessel 168) first engages the lumen 102 of the guidewire tube 88 at the tapered tip 28 of the distal tube 44 followed by exiting of the guidewire 154 from the lumen 102 at the proximal end 108 of the guidewire tube 88 at the guidewire tube exit region 46. A high pressure fluid source 156 and a high pressure fluid pump 158 connect as shown to the manifold 12 via the threaded high pressure connection port 26 by a threaded nut 160 or optionally by a direct connection. An optional exhaust regulator 162 and a collection chamber 164 connect to the threaded branch end 22 of the exhaust branch 20 of the manifold 12 by a Luer fitting 166, as shown.

FIG. 18 is a side view of the rapid exchange fluid jet thrombectomy device 10 in the performance of the method of use thereof, with particular attention given to the distal region of the distal tube 44 including the flexible tapered tip 28 positioned in a blood vessel 168 at a site of a thrombotic deposit or lesion 170. Multiple jet streams of high velocity fluid jet flows 138 of saline (or other suitable fluid) are shown being emitted in a proximal direction from the fluid jet emanator 96 to impinge upon and carry away thrombotic deposits or lesions 170. Other fluid jet emanators can be incorporated within the distal portion of the distal tube 44 as an alternative to the fluid jet emanator 96 illustrated in this figure to emanate or emit one or more high velocity fluid jet flows 138 distally along or near the longitudinal axis of the distal tube 44 to accomplish the same purpose as that described for the fluid jet emanator 96. The high velocity fluid jet flows 138 of saline pass outwardly through the outflow orifices 48a-48n in a radial direction creating cross stream jets 174 (lower velocity jets) directed outwardly toward the wall of the blood vessel 168 and are influenced by the low pressure at the inflow orifices 50a-50n to cause the cross stream jets 174 to flow circumferentially and distally to impinge on, provide drag forces on, and break up thrombotic deposits or lesions 170 and to, by entrainment, urge and carry along the particles of thrombotic deposits or lesions 170 through the inflow orifices 50a-50n, a relatively low pressure region, into the high velocity fluid jet flows 138 where the thrombus is further macerated into microscopic particles, and then into the distal tube lumen 94 (FIG. 16). A certain portion of this macerated debris which is mixed with fresh saline is removed through the distal tube lumen 94 and a certain portion flows back out the outflow orifices 48a-48n and recirculates to break up more debris which is returned to the inflow orifices 50a-50n. In this way, much more fluid flow circulates through the system than is injected through the jet orifices 126a-126n. For purposes of illustration and example, three to ten times more flow circulates through the system than is delivered by the jet orifices 126a-126n. The entrainment through the inflow orifices 50a-50n is based on entrainment by the high velocity fluid jet flows 138. The outflow is driven by internal pressure which is created by the high velocity fluid jet flows 138 and the fluid entrained through the inflow orifices 50a-50n. Enhanced clot removal is attainable because of the recirculation pattern established between outflow and inflow orifices 48a-48n and 50a-50n, which creates a flow field that maximizes drag force on wall-adhered thrombus. Since the entrained thrombus is macerated into microscopic particles, those particles that exit the outflow orifices 48a-48n are not of sufficient size to significantly block the distal circulation, and will be re-entrained into the inflow orifices 50a-50n at a high rate. In a no-flow situation or when flow is stopped with another device such as an occlusive balloon, then material can be recirculated and rediluted until all that remains is saline and all particles are removed.

Figure 19:
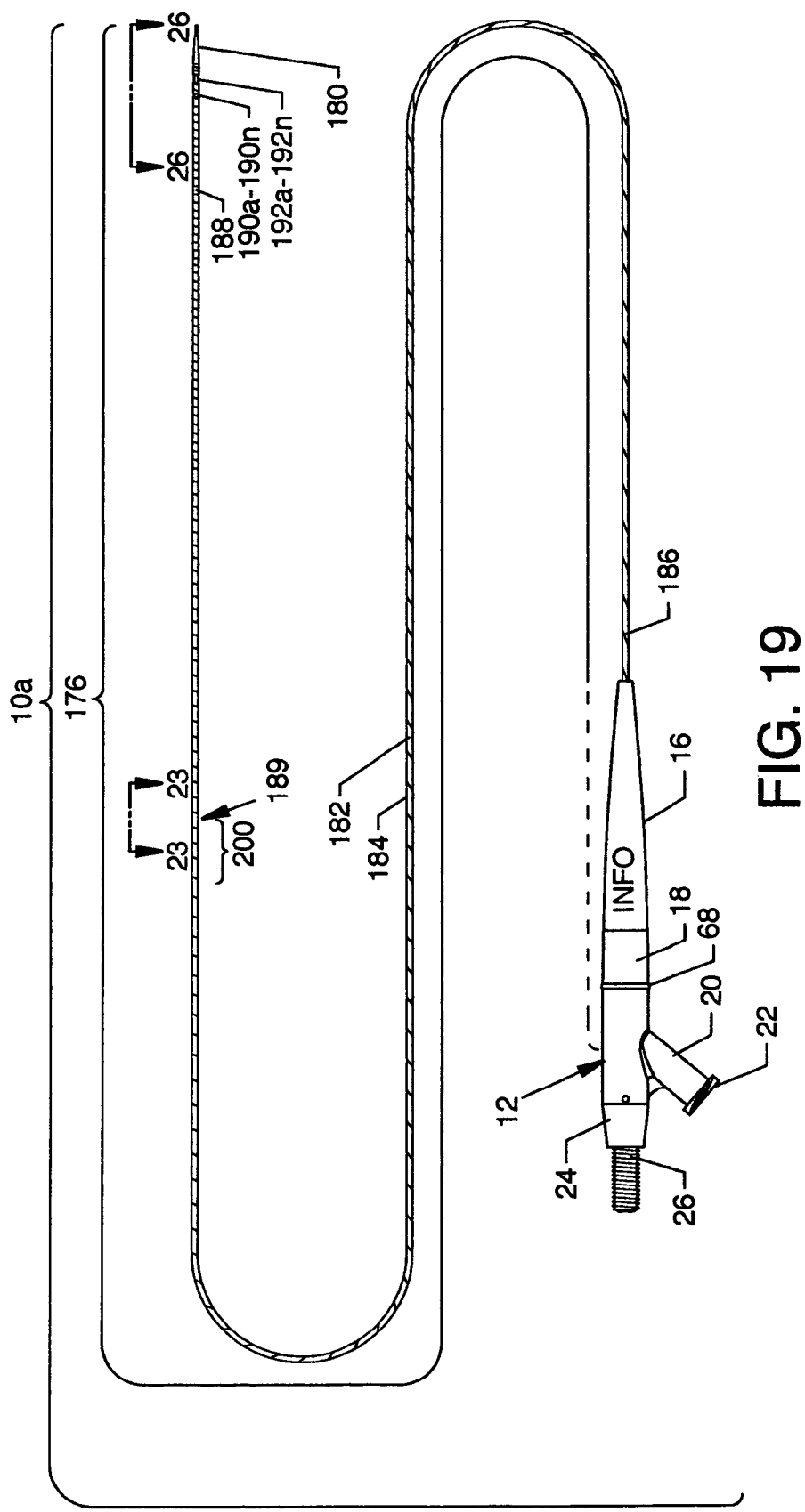
FIG. 19, a first alternative embodiment, is a plan view of the readily visible components of a rapid exchange fluid jet thrombectomy device including a manifold with a strain relief and a catheter extending distally from the strain relief.

FIG. 19, a first alternative embodiment, is a plan view of the readily visible components of a rapid exchange fluid jet thrombectomy device 10a employing many components and teachings of the first embodiment including the manifold 12 and also including a catheter 176 extending from the manifold 12.

The catheter 176 comprises a unitary, continuous, elongated, tubular structure containing or hosting various components and serving as an exhaust path extending distally from inside the manifold 12 and through the strain relief 16 and terminating at a tapered tip 180. The catheter 176 includes a full length spiral metal tube 182 which can be laser cut or otherwise suitably fashioned. The pitch of the cut can be progressively or otherwise varied along the length of the spiral metal tube 182. The use of the spiral metal tube 182, instead of the easily kinkable, stiff, projecting metal tube of previous designs, preserves the excellent pushability and torqueability of previous designs, but is less kinkable and more flexible than previous designs. The spiral cut can be progressively transitioned in pitch from distal to proximal to produce a continuous transition from flexible to stiff which maximizes the pushability and "feel" of the catheter 176. Although the pitch of the cut is shown as uniformly progressive, the spiral cut along the spiral metal tube 182 can be of various configurations to achieve the desired property. During manufacturing, the length of the spiral metal tube 182 can be extended or shortened anywhere along the length of the catheter 176, or the pitch can be configured to provide a desired mechanical property. A polymer jacket 184, which can be transparent and which can be in the form of a shrink tube, encompasses the spiral metal tube 182, thus creating a leak-free tubular structure, as well as adding mechanical and lubricious properties to the catheter 176. For example and for purposes of illustration, a uniformly progressive pitch of the spiral metal tube 182 can be seen through the polymer jacket 184 if a transparent polymer is incorporated, starting with a wide pitch shown at 186 at the strain relief 16 transitioning to a close pitch shown at 188 at the distal end of the spiral metal tube 182. A guidewire tube exit region 189 is located along the catheter 176, as later described in detail. Also located near the tapered tip 180 are a plurality of outflow orifices 190*a*-190*n* and a plurality of inflow orifices 192*a*-192*n*.

Figure 20:
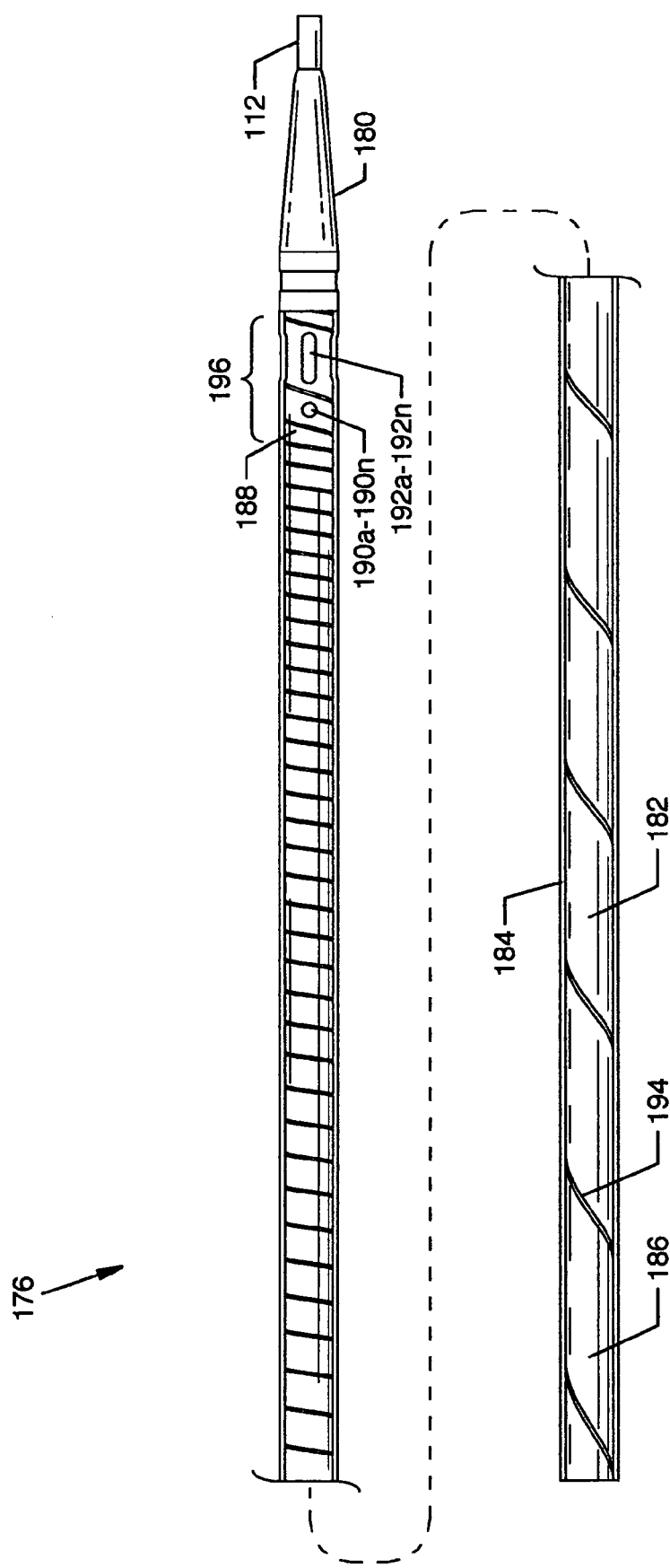
FIG. 20 is a separated side view of the catheter.

FIG. 20 is a separated side view of the catheter 176. Provided that the material of the polymer jacket 184 encasing the spiral metal tube 182 is transparent, the spiral metal tube 182 is easily viewed therethrough. A spiral cut 194 extends along and about the spiral metal tube 182 where the spiral cut 194 defines a progressive pitch decreasing between the wide pitch shown at 186 and the close pitch shown at 188. As in the first embodiment, the polymer jacket 184 closely aligns over and about the spiral metal tube 182. The spiral cut 194, which can be produced by a laser cutting tool or other suitable fashioning methods, can be incorporated to produce a continuous spiral metal tube 182. A wide pitch region 196 is included closely juxtaposing and distal to the close pitch 188 for accommodation of the outflow orifices 190*a*-190*n* and the inflow orifices 192*a*-192*n*. Also shown is the tip extension tube 112 extending distally from the tapered tip 180.

Figure 21:
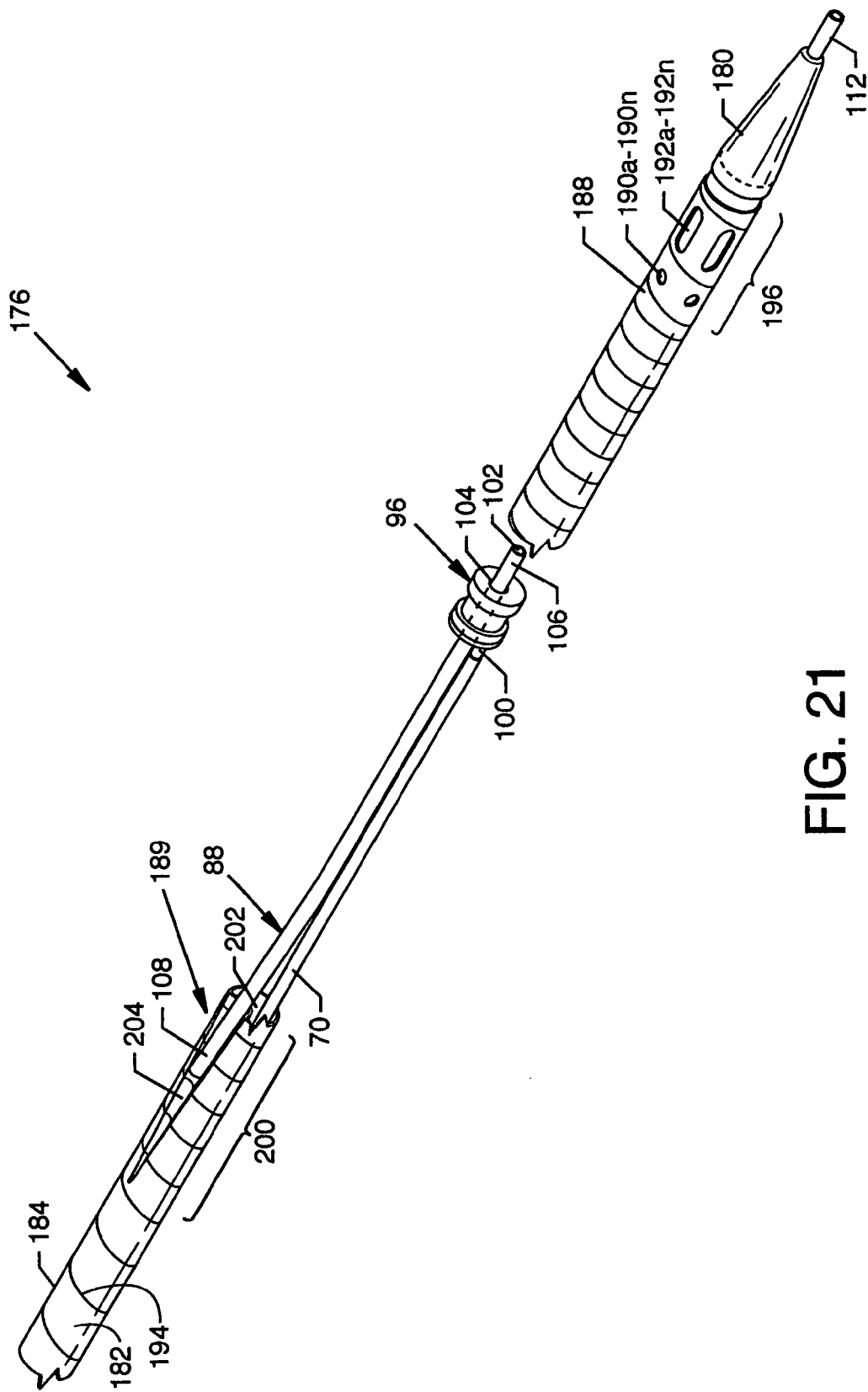
FIG. 21 is an exploded and separated isometric view of the components of the catheter from and including a formed tubular portion of a spiral metal tube to the tapered tip, some components being foreshortened with respect to length for the purpose of illustration and clarity.

FIG. 21 is an exploded and separated isometric view of the components of the catheter 176 from and including a formed tubular portion 200 of the spiral metal tube 182 to the tapered tip 180, some components being foreshortened with respect to length for the purpose of illustration and clarity. The shown portion of the catheter 176 includes the spiral metal tube 182, the polymer jacket 184, the flexible guidewire tube 88 of polymer, the high pressure tube 70, the fluid jet emanator 96, and other components within, along, and about the catheter 176.

Figure 26:
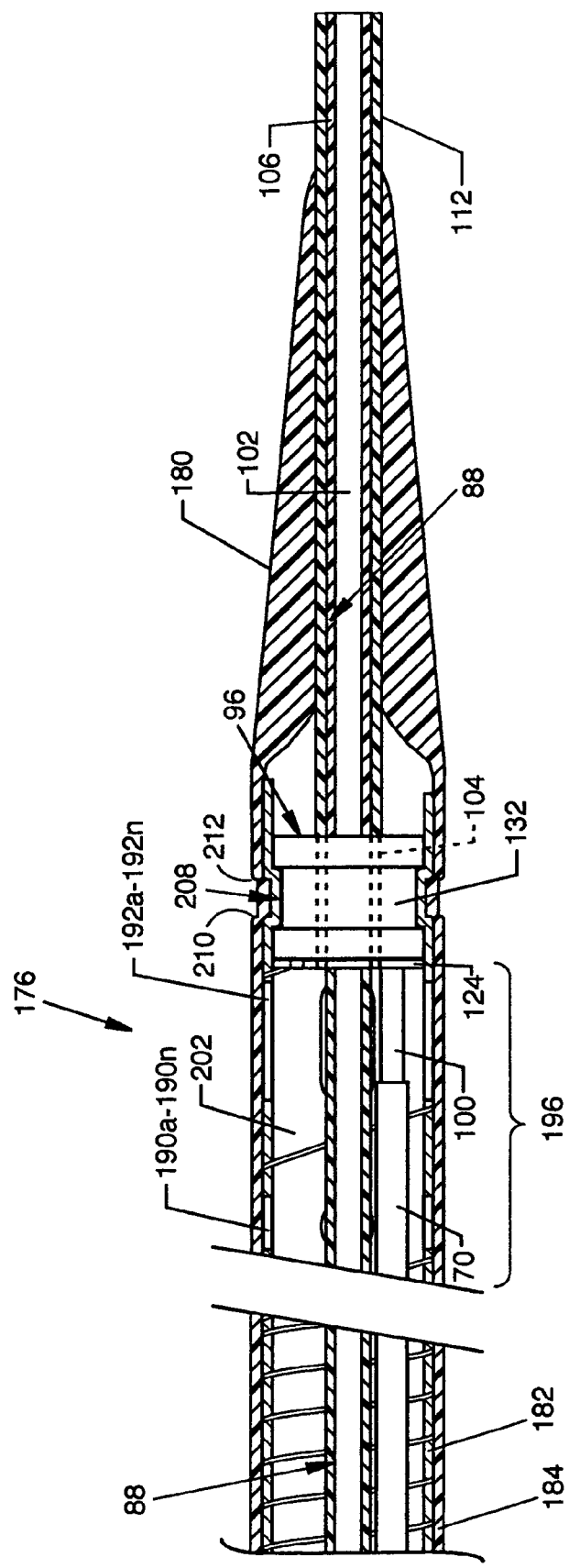
FIG. 26 is a cross section view of the distal portion of the catheter including the tapered tip along line 26-26 of FIG. 19.

The high pressure tube 70 with a lumen 90 (FIG. 23) extends from the manifold 12, as previously described, through a lumen 202 in the spiral metal tube 182, and connectively terminates at the fluid jet emanator 96. The high pressure tube 70 also extends through and can be supportingly attached to the interior wall of the metal spiral tube 182, such as by welding or other suitable means, in lieu of incorporating a tube support ring. The fluid jet emanator 96, as well as the distal end 100 of the high pressure tube 70, locate distally in the lumen 202 of the spiral metal tube 182, as shown in FIG. 26. The distal end of the spiral metal tube 182 is swaged about and accommodated by the annular groove 132 of the fluid jet emanator 96, thereby forcibly and mutually fixing the fluid jet emanator 96 to the spiral metal tube 182 and securing the fluid jet emanator 96 with respect to the outflow orifices 190*a*-190*n* and the inflow orifices 192*a*-192*n*, as best shown in FIG. 26, thereby eliminating the use of a radiopaque marker band as a securing device. The guidewire tube 88, having a lumen 102 and a proximal end 108, is securely accommodated by a crescent-shaped truncated and rounded slot 204 at the formed tubular portion 200 and secures thereto by adhesive, if required, and extends distally from the formed tubular portion 200 at the guidewire tube exit region 189 through an orifice 206 (FIG. 22), where the orifice 206 transitions between the distal end of the truncated and rounded slot 204 and the lumen 202 of the spiral metal tube 182, to then continue through the passageway 104 in the fluid jet emanator 96, and further through the distal portion of the lumen 202 of the spiral metal tube 182, where the distal portion 106 of the guidewire tube 88 terminates securely, such as by heat bonding or other suitable means, within a soft tip extension tube 112 which is flexible and which is located in and extends distally beyond the general body of the tapered tip 180. Heat can be applied to form the tapered tip 180 of increasingly flexible shape in a distal direction at the end of the catheter 176, as well as to engagingly secure the distal end portion 106 of the guidewire tube 88 to and within the tip extension tube 112 of the tapered tip 180. The tapered tip 180 may also be formed through a cold draw-down process or may be physically attached through adhesives or polymer reintegration. The plurality of outflow orifices 190*a*-190*n* and the plurality of inflow orifices 192*a*-192*n* spaced distal to the outflow orifices 190*a*-190*n* are included around and about the distal region of the catheter 176.

Figure 22:
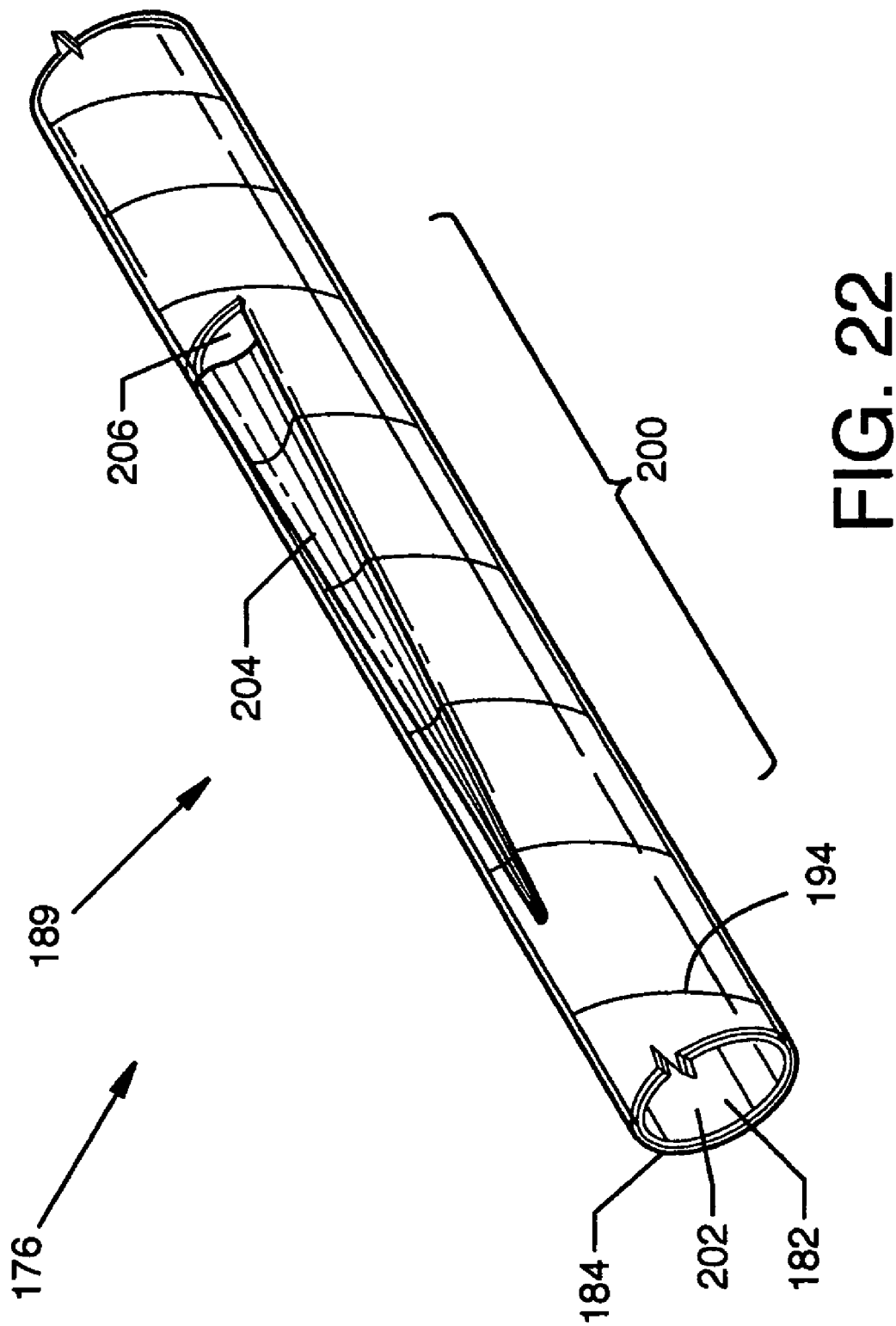
FIG. 22 is an isometric view of the portion of the catheter containing the guidewire tube exit region.
Figure 23:
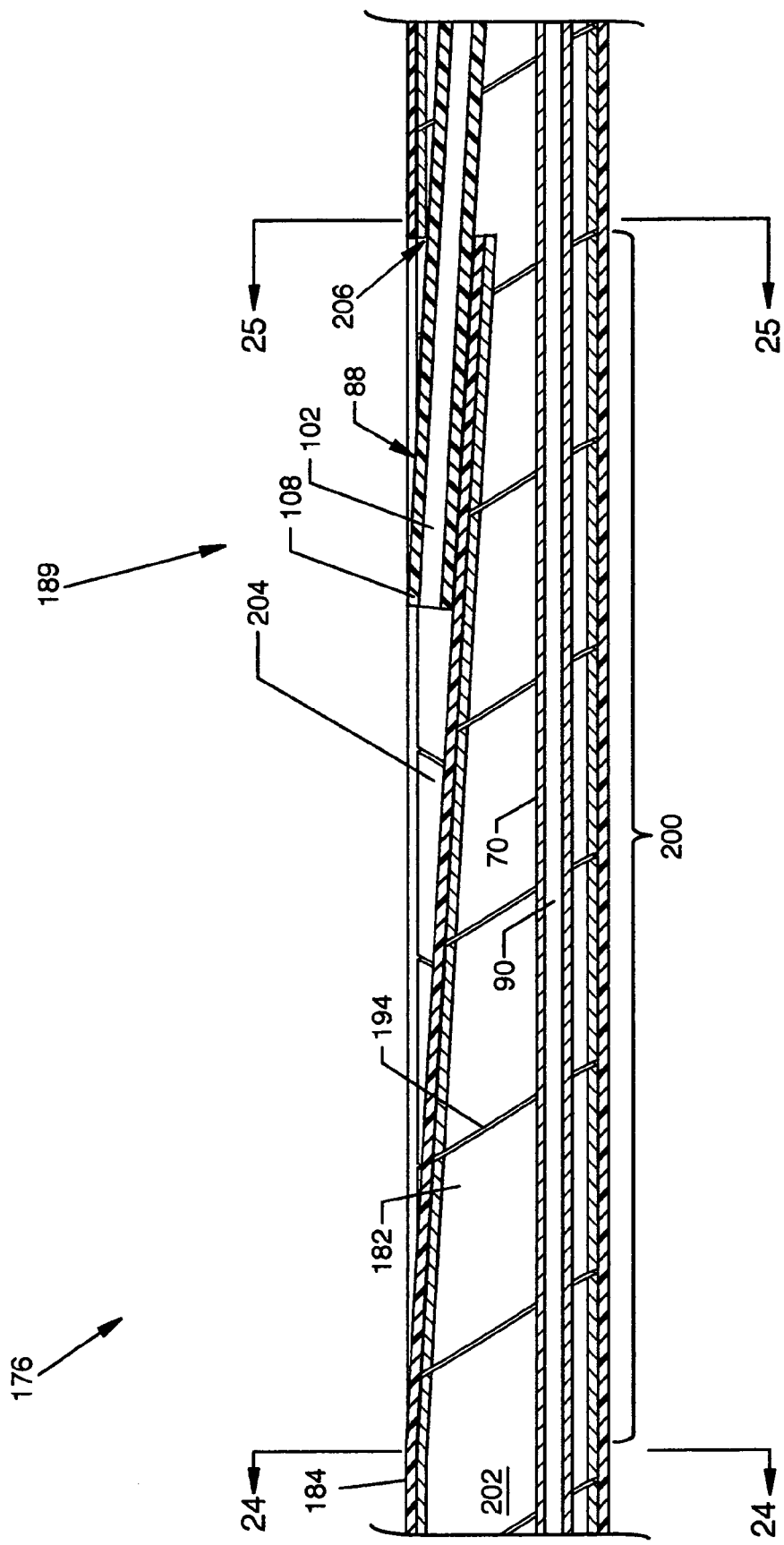
FIG. 23 is a cross section view of the catheter along line 23-23 of FIG. 19.

FIG. 22 is an isometric view of the portion of the catheter 176 containing the guidewire tube exit region 189 which is produced by the formed tubular portion 200 of the spiral metal tube 182. The formed tubular portion 200 includes geometry in the form of a truncated and rounded slot 204 of decreasing depth in a proximal direction which accommodates the guidewire tube 108 (FIG. 21). The truncated and rounded slot 204 is substantially formed in the shape of a nearly full semi-circular arc at the extreme distal end of the formed tubular portion 200. The arc, while the radius remains constant, is decreased progressing proximally from the extreme distal end of the formed tubular portion 200 to provide for angled transitional accommodation of the guidewire tube 88, as shown in FIGS. 21 and 23. Other transitional accommodation for routing of the guidewire tube 88 is offered by the orifice 206, previously mentioned in connection with FIG. 21. Lumen 202 interior to the spiral metal tube 182 accommodates the high pressure tube 70 and also functions as the overall effluent exhaust path.

FIG. 23 is a cross section view of the catheter 176 along line 23-23 of FIG. 19. Shown in particular is the guidewire tube exit region 189, the formed tubular portion 200, the proximal end 108 of the guidewire tube 88, and the guidewire tube 88 at the guidewire tube exit region 189. The proximal end 108 of the guidewire tube 88 is accommodated by the truncated and rounded slot 204 and a portion of the co-located overlying polymer jacket 184 to which it is secured by an adhesive, by welding, or other such suitable method, and by the orifice 206 at the distal end of the truncated and rounded slot 204. The proximal end 108 of the guidewire tube 88 is of such length that the outer profile of the catheter 176 is not exceeded so as to maintain the desired minimal catheter profile. The portion of the truncated and rounded slot 204 which is not occupied by the proximal end 108 of the guidewire tube 88 and which is proximal to the proximal end 108 can also be utilized to accommodate a guidewire without structure interference. Also illustrated is the high pressure tube 70 having the lumen 90 passing through the lumen 202. Lumen 202 of the spiral metal tube 182 functions as an exhaust route extending the length of the catheter 176.

Figure 24:
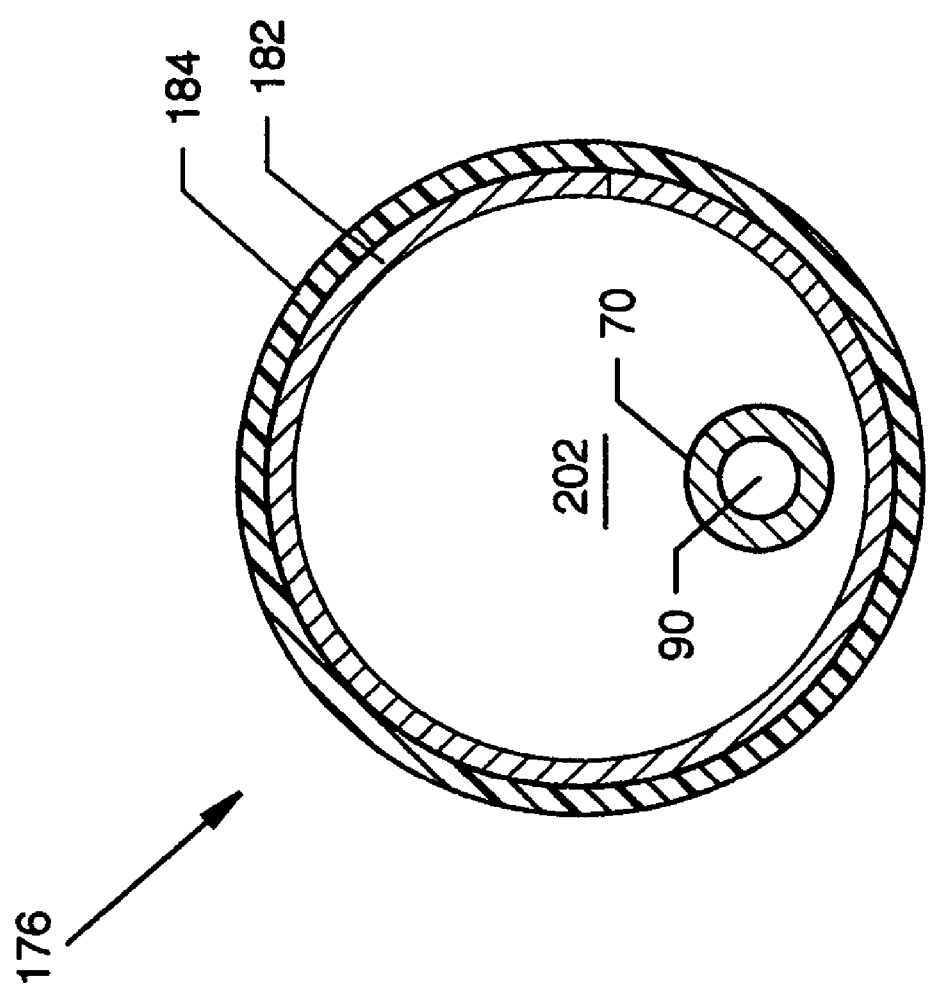
FIG. 24 is a cross section view of the catheter along line 24-24 of FIG. 23.

FIG. 24 is a cross section view of the catheter 176 along line 24-24 of FIG. 23. Illustrated in particular is the lumen 202 of the spiral metal tube 182 which functions as an exhaust route through the catheter 176 with minimal obstructions or restrictions therein.

Figure 25:
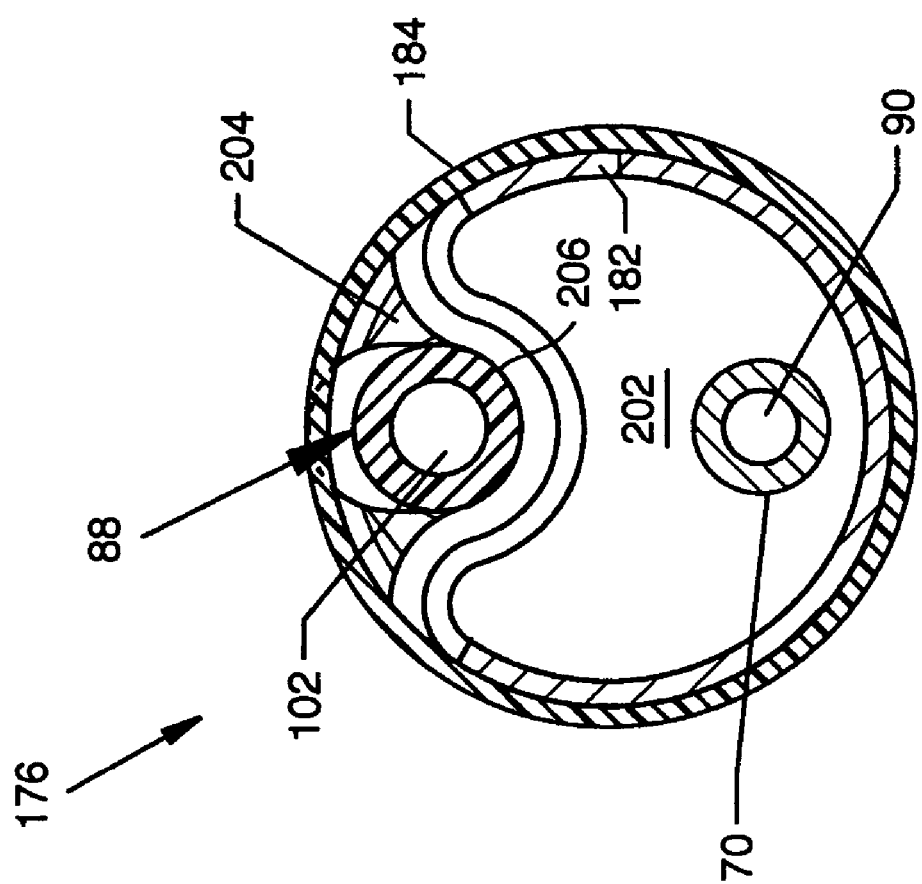
FIG. 25 is a cross section view of the catheter along line 25-25 of FIG. 23.

FIG. 25 is a cross section view of the catheter 176 along line 25-25 of FIG. 23. Illustrated in particular is the alignment and accommodation of the guidewire tube 88 in the truncated and rounded slot 204 at the formed tubular portion 200 of the spiral metal tube 182. Also illustrated is the lumen 202 which functions as an exhaust route through the catheter 176 with minimal obstructions or restrictions therein.

FIG. 26 is a cross section view of the distal portion of the catheter 176 including the tapered tip 180 along line 26-26 of FIG. 19. The radiopaque marker bands of the first embodiment are not incorporated for securing the fluid jet emanator 96 to the spiral metal tube 182 of the catheter 176 in lieu of another attachment method in which a swage 208 is incorporated. Swaging force is applied over and about the distal portion of the spiral metal tube 182 to cause frictional annular engagement of a small portion of the spiral metal tube 182 with all or part of the annular groove 132 of the fluid jet emanator 96. The swaged engagement of the spiral metal tube 182 over and about the fluid jet emanator 96 is not abrupt in nature with respect to the smooth surface of the spiral metal tube 182. The polymer jacket 184, which overlies the swage 208, can follow the contour of the swage 208, wherein opposed curved annular edges 210 and 212 are formed adjacent to the edges of the swage 208. The curved annular edges 210 and 212 are generally smooth in nature and thereby aid in unimpeded and smooth distal or proximal transition of the catheter 176 within a vein, artery or the like.

Structure is provided to nurture and aid introduction of and passage of the distal portion of the catheter 176 through blood vessels to the sites of thrombotic deposits or lesions. The tapered tip 180, as opposed to a rounded but nontapered tip, can part and more easily penetrate thrombotic deposits or lesions during insertional travel in a distal direction instead of advancing or pushing such thrombotic deposits or lesions distally. The decreasing diameter in a distal direction of the tapered tip 180 also allows for increasing flexibility to negotiate and pass through tortuous vascular paths. The portion of the catheter 176 which immediately follows the tapered tip 180 on a tortuous negotiation and passage is influenced by the supportive structure of the spiral metal tube 182, which offers reinforcement to form and contribute to maintaining the diameter of the catheter 176 along the entire catheter 176 against bending or collapsing due to tortuous paths or negative pressures, especially in the regions in close proximity to or including the inflow orifices 192a-192n and the outflow orifices 190a-190n. Such support allows the use of thinner wall dimension for the catheter 176 to allow for a larger and more effective and efficiently sized lumen 202, as well as contributes to a lesser sized outer diameter. Such support also contributes to supportively maintaining the diameter and overall shape of the catheter 176 when it is pushed or advanced along a vein or other vessel, as well as provides torsional support.

Figure 27:
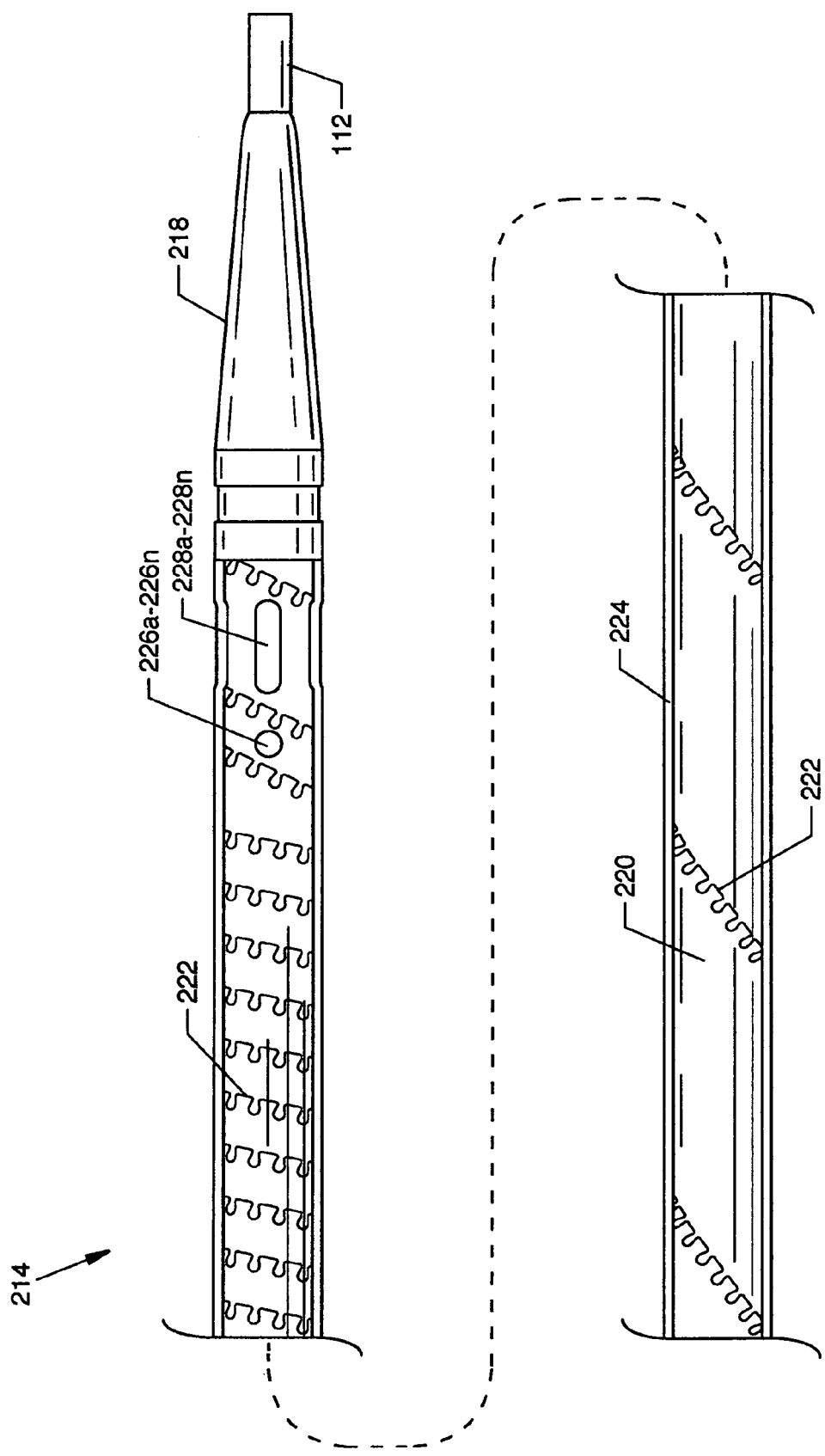
FIG. 27, a second alternative embodiment, is a separated plan view of a catheter showing the proximal and distal ends; and, FIG. 28 is a view of a section of the catheter of FIG. 27 showing the interlocking cut features on an enlarged scale.

FIG. 27, a second alternative embodiment, is a separated plan view of a catheter 214 showing the proximal and distal ends thereof and employing many components and teachings of the first embodiment and especially of the first alternative embodiment. The catheter 214 also incorporates a guidewire tube exit region (not shown) similar in shape and function to the guidewire tube exit region 189 of the first alternative embodiment, and a formed tubular portion (not shown) similar in shape and function to the formed tubular portion 200 of the first alternative embodiment. The catheter 214 can be employed into use with the manifold 12 as a replacement for the catheter 14 of the rapid exchange fluid jet thrombectomy device 10 or as a replacement for the catheter 176 of the rapid exchange fluid jet thrombectomy device 10a.

The catheter 214 comprises a unitary, continuous, elongated, tubular structure which closely replicates the catheter 176 of the first alternative embodiment incorporating the internal structure thereof including the high pressure tube 70 and the swaged engagement of the spiral metal tube 182 over and about the fluid jet emanator 96 and is comprised generally of tubular structure containing or hosting various components, such structure being a continuous one-piece tube including a tapered tip 218 and a tip extension tube 112 which are constructed and utilized in the same manner as that described in connection with the first alternative embodiment. The catheter 214, which is an assembly, includes a full length interlocking spiral metal tube 220 having an interlocking cut 222 which can be laser cut or otherwise suitably fashioned. The interlocking cut 222 differs from the spiral cut 84 of the first embodiment and the spiral cut 194 of the first alternative embodiment, both of which are plain linear cuts having no coupling or interlocking features extending across the cuts. The interlocking spiral metal tube 220 replaces the spiral metal tube 182, such as is used in the first alternative embodiment. The interlocking structure of the interlocking spiral metal tube 220 is shown in detail in FIG. 28.

The pitch of the interlocking cut 222 can include groups of constant pitch or can be of progressive pitch as shown or otherwise varied along the length of the interlocking spiral metal tube 220. The use of the interlocking spiral metal tube 220 instead of the easily kinkable, stiff, projecting metal tube of previous designs preserves the excellent pushability and torqueability of previous designs, but is less kinkable and more flexible than previous designs. Additionally, the incorporation of the interlocking cut 222 further increases torsional and torqueability control and response for use where rotation of the catheter is made in either or both clockwise and counterclockwise directions during insertion and maneuvering to travel along a tortuous vascular path or through regions of thrombus. For example, the use of the previously described catheters may favor one direction rotation (clockwise for example) in terms of lag when maneuvering in the vasculature although either direction of rotation is suitable, as a spiral metal tube such as spiral metal tube 182 exhibits the characteristics of a closely or tightly wound spring. Rotation of the spiral metal tube 182 in a clockwise direction produces corresponding movement along the spiral metal tube 182 and catheter 176 almost instantly at the distal end, whereas rotation in a counterclockwise direction may cause a lag in movement as the spiral metal tube 182 may exhibit characteristics not unlike that of a closely wound spring; i.e., twisting of one end in one direction produces a directly corresponding movement at the opposite end of the spring with little lag, whereas twisting in the opposite direction laggingly "unwinds" the closely wound spring, and thus exhibits a delayed and unproportional corresponding movement. The interlocking feature of the interlocking spiral metal tube 220 promotes more timely rotational and torque response and minimizes and greatly reduces lag in both clockwise and counterclockwise directions where twisting of the catheter tube 214 is utilized for maneuvering through the vasculature.

The interlocking cut 222 can be progressively transitioned in pitch from distal to proximal to produce a continuous transition from flexible to stiff which maximizes the pushability and "feel" of the catheter 214. Although the pitch of the interlocking cut 222 is shown as groups of progressive pitch, the interlocking cut along the interlocking spiral metal tube 220 can be of various configurations to achieve the desired property. During manufacturing, the length of the interlocking spiral metal tube 220 can be extended or shortened anywhere along the length of the catheter 214 or the pitch can be configured to provide a desired mechanical property. A polymer jacket 224, which can be transparent and which can be in the form of a shrink tube, encompasses the interlocking spiral metal tube 220, thus creating a leak-free tubular structure, as well as adding mechanical and lubricious properties to the catheter 214. For example and for purposes of illustration, the uniformly progressive pitch of the interlocking spiral metal tube 220 can be seen through the polymer jacket 224, if a transparent polymer is incorporated. Also located near the tapered tip 218 are a plurality of outflow orifices 226a-226n and a plurality of inflow orifices 228a-228n.

Figure 28:
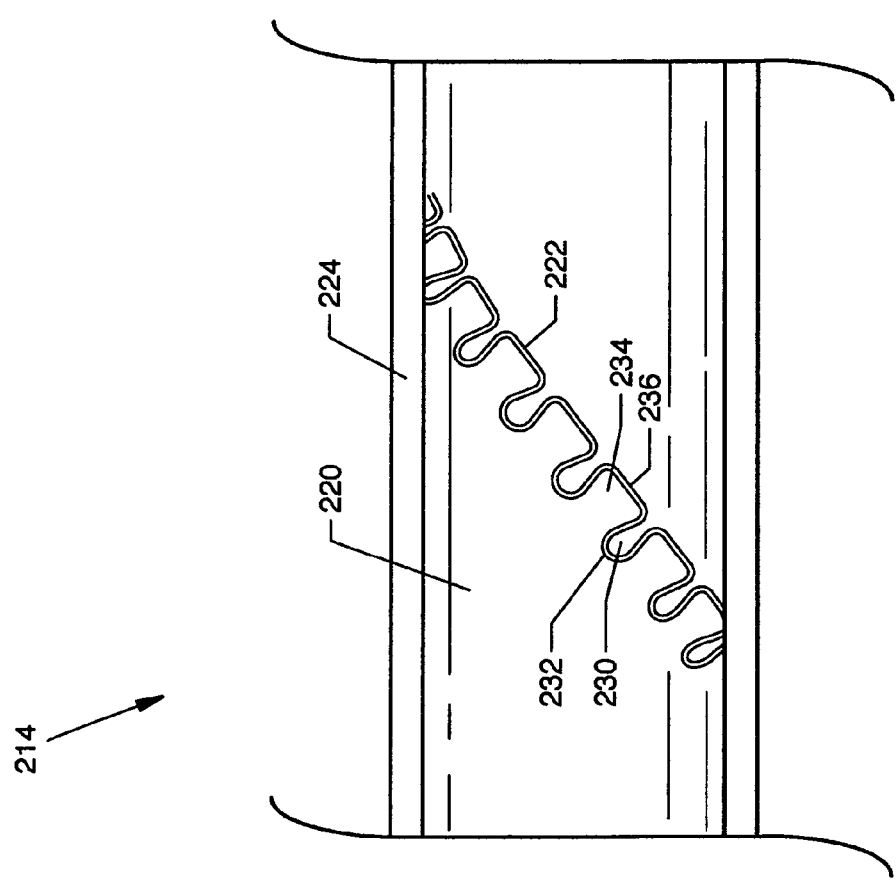

FIG. 28 is a view of a section of the catheter 214 of FIG. 27 showing the interlocking cut features on an enlarged scale. The interlocking cut 222 in the interlocking spiral metal tube 220 defines sets of repeating and continuous spaced and interlocking nodes and node receptors which mutually and interlockingly and couplingly loosely engage each other respectively across the interlocking cut 222 to provide communication therebetween. One such set includes a node 230 which engages a node receptor 232, the shape of the node 230 corresponding to the shape of the node receptor 232. Another such set includes a node 234 which engages a node receptor 236, the shape of the node 234 corresponding to the shape of the node receptor 236. The nodes 230 and 234 are free to flex within the confines of the node receptors 232 and 236, respectively, to provide for flexibility along the interlocking spiral metal tube 220 and polymer jacket 224 which form the greater portion of the catheter 214.

Multiple embodiments have been incorporated into the rapid exchange fluid jet thrombectomy device where many components of such are exchangeable with other components during manufacturing, thereby allowing multiple combinations of components and features described herein according to the teachings and scope of the invention.

Further, other attributes of the present invention exist in addition to the many mentioned in the foregoing description of the preferred embodiments. For example, each of the several embodiments of the present invention has the capacity of being utilized to inject medicinal or detectable fluids, drugs and the like into the body from a supply source into the manifold and thence into and through the catheter to the fluid jet emanator, then through the jet orifices, and thence through the outflow orifices to a thrombus site.

Also, the structure and teachings of the preceding embodiments can be adopted without the inclusion of a guidewire tube exit region and a formed tubular portion to provide a medical tube of general utility formed of a polymer-jacketed spiral metal tube with the spiral being a basic continuous spiral which may occur in groups of constant pitch or in progressive pitch along the length of the spiral metal tube. Further, the polymer-jacketed spiral metal tube can include a Teflon® or similar polymer interior lining, thereby adapting it to multiple uses, including use as a guidewire tube, the liner serving to aid in guidewire compatibility and trackability along the interior of the spiral metal tube. Still further, instead of the spiral being a basic continuous spiral, the spiral can be an interlocking structure spiral which may occur in groups of constant pitch or in progressive pitch along the length of the spiral metal tube. The interlocking structure spiral provides superior torqueability and other handling characteristics. Again, a Teflon® or similar polymer lining can be provided. The medical tubes of general utility just described have many applications, including use in lieu of catheters in existing thrombectomy catheter devices.

Mode of Operation

The mode of operation of the rapid exchange fluid jet thrombectomy device 10a is closely replicated by the mode of operation described for the rapid exchange fluid jet thrombectomy device 10 where the catheter 14 and associated and related components of the rapid exchange fluid jet thrombectomy device 10 are replaced by the catheter 176 and associated and related components of the rapid exchange fluid jet thrombectomy device 10a.

Various modifications can be made to the present invention without departing from the apparent scope hereof.

It is claimed:

1. A rapid exchange fluid jet thrombectomy device, comprising:
   a. a manifold including a strain relief; and,
   b. a catheter extending distally from the manifold, through the strain relief, and terminating in a tapered tip, the catheter including:
      (1) an elongated tubular structure which serves as an exhaust path for effluent from the tapered tip to the manifold, at least a portion of the elongated tubular structure being composed of a spiral metal tube formed of a metal tube having a spiral cut along its length, the spiral metal tube being surrounded by a polymer jacket, the elongated tubular structure also having a distal portion near the tapered tip, said distal portion having at least one inflow orifice and at least one outflow orifice, and
      the spiral cut decreases in pitch from a spiral metal tube proximal end toward the distal portion with the spiral metal tube increasing in flexibility toward the distal portion, and the spiral cut increases in pitch at the distal portion from a position proximal to the outflow orifice to a position distal to the inflow orifice with the spiral metal tube decreasing in flexibility at the distal portion;
      (2) a high pressure tube extending through the elongated tubular structure and having a proximal end anchored within the manifold and a distal end located adjacent to the tapered tip; and
      (3) a fluid jet emanator attached to the high pressure tube at the distal end of the high pressure tube.

2. The rapid exchange fluid jet thrombectomy device as defined in claim 1, wherein the spiral cut is a basic continuous spiral cut having regions of different pitch along the length of the spiral metal tube.

3. The rapid exchange fluid jet thrombectomy device as defined in claim 1, wherein the spiral cut is an interlocking structure spiral cut having a progressively decreasing pitch from the proximal end of the spiral metal tube to the distal end of the spiral metal tube.

4. The rapid exchange fluid jet thrombectomy device as defined in claim 1, wherein the elongated tubular structure comprises a proximal tube formed of the spiral metal tube, an intermediate tube, and a distal tube joined to each other.

5. The rapid exchange fluid jet thrombectomy device as defined in claim 4, further including a guidewire exit region formed at the area where the intermediate tube joins the distal tube.

6. The rapid exchange fluid jet thrombectomy device of claim 1, wherein the manifold includes an adhesive port, and an adhesive is delivered to the spiral metal tube within the manifold to engage the spiral metal tube with the manifold.

7. The rapid exchange fluid jet thrombectomy device of claim 6, wherein the adhesive is delivered to the polymer jacket and overlies the polymer jacket.

8. The rapid exchange fluid jet thrombectomy device of claim 1, wherein a raised ring extends around the manifold.

9. A rapid exchange fluid jet thrombectomy device comprising:
   a. a manifold including a strain relief; and,
   b. a catheter extending distally from the manifold, through the strain relief, and terminating in a tapered tip, the catheter including:
      (1) an elongated tubular structure which serves as an exhaust path for effluent from the tapered tip to the manifold, at least a portion of the elongated tubular structure being composed of a spiral metal tube formed of a metal tube having a spiral cut along its length, the spiral metal tube being surrounded by a polymer jacket, the elongated tubular structure also having a distal portion near the tapered tip, said distal portion having at least one inflow orifice and at least one outflow orifice, wherein the spiral cut includes an interlocking structure having regions of different pitch along the length of the spiral metal tube, and the interlocking structure includes coupling features that mechanically interfit with corresponding coupling features on opposed surfaces of the spiral metal tube along the spiral cut;

(2) a high pressure tube extending through the elongated tubular structure and having a proximal end anchored within the manifold and a distal end located adjacent to the tapered tip; and, (3) a fluid jet emanator attached to the high pressure tube at the distal end of the high pressure tube.

10. The rapid exchange fluid jet thrombectomy device of claim 9, wherein the manifold includes an adhesive port, and an adhesive is delivered to the spiral metal tube within the manifold to engage the spiral metal tube with the manifold.

11. The rapid exchange fluid jet thrombectomy device of claim 10, wherein the adhesive is delivered to the polymer jacket and overlies the polymer jacket.

12. The rapid exchange fluid jet thrombectomy device of claim 9, wherein a raised ring extends around the manifold.

13. The rapid exchange fluid jet thrombectomy device as defined in claim 9, wherein the spiral cut is a basic continuous spiral cut having regions of different pitch along the length of the spiral metal tube.

14. The rapid exchange fluid jet thrombectomy device as defined in claim 9, wherein the spiral cut is a basic continuous spiral cut having a progressively decreasing pitch from the proximal end of the spiral metal tube to the distal end of the spiral metal tube.

15. The rapid exchange fluid jet thrombectomy device as defined in claim 9, wherein the elongated tubular structure comprises a proximal tube formed of the spiral metal tube, an intermediate tube, and a distal tube joined to each other.

16. The rapid exchange fluid jet thrombectomy device as defined in claim 15, further including a guidewire exit region formed at the area where the intermediate tube joins the distal tube.

* * * * *

UNITED STATES PATENT AND TRADEMARK OFFICE
CERTIFICATE OF CORRECTION

| | | |
|---|---|---|
| PATENT NO. | : 7,879,022 B2 | Page 1 of 1 |
| APPLICATION NO. | : 11/096592 | |
| DATED | : February 1, 2011 | |
| INVENTOR(S) | : Bonnette et al. | |

It is certified that error appears in the above-identified patent and that said Letters Patent is hereby corrected as shown below:

IN THE CLAIMS:

Column 22, Line 41, Claim 3, delete "metal tube to the distal end" and insert -- metal tube to a distal end --, therefor.

Signed and Sealed this
Third Day of April, 2012

David J. Kappos
*Director of the United States Patent and Trademark Office*